US009809569B2

(12) United States Patent
Yamada et al.

(10) Patent No.: US 9,809,569 B2
(45) Date of Patent: Nov. 7, 2017

(54) PROCESS FOR PRODUCING HETEROCYCLIC COMPOUND

(71) Applicant: Takeda Pharmaceutical Company Limited, Osaka (JP)

(72) Inventors: Masatoshi Yamada, Osaka (JP); Sayuri Hirano, Osaka (JP); Ryoji Tsuruoka, Osaka (JP); Mitsuhisa Yamano, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/125,299

(22) PCT Filed: Mar. 13, 2015

(86) PCT No.: PCT/JP2015/057541
§ 371 (c)(1),
(2) Date: Sep. 12, 2016

(87) PCT Pub. No.: WO2015/137496
PCT Pub. Date: Sep. 17, 2015

(65) Prior Publication Data
US 2017/0081305 A1   Mar. 23, 2017

(30) Foreign Application Priority Data
Mar. 14, 2014 (JP) ................. 2014-052809

(51) Int. Cl.
| C07D 401/04 | (2006.01) |
| C07D 211/60 | (2006.01) |
| C07D 211/78 | (2006.01) |
| C07F 17/02 | (2006.01) |
| B01J 31/24 | (2006.01) |
| C07F 9/50 | (2006.01) |
| C07F 15/00 | (2006.01) |
| B01J 31/22 | (2006.01) |

(52) U.S. Cl.
CPC ........ *C07D 401/04* (2013.01); *B01J 31/2226* (2013.01); *B01J 31/2295* (2013.01); *B01J 31/2409* (2013.01); *B01J 31/2452* (2013.01); *C07D 211/60* (2013.01); *C07D 211/78* (2013.01); *C07F 9/5027* (2013.01); *C07F 15/0046* (2013.01); *C07F 17/02* (2013.01); *B01J 2231/645* (2013.01); *B01J 2531/0205* (2013.01); *B01J 2531/0263* (2013.01); *B01J 2531/0266* (2013.01); *B01J 2531/821* (2013.01); *B01J 2531/822* (2013.01); *B01J 2531/824* (2013.01); *B01J 2531/827* (2013.01); *B01J 2531/842* (2013.01); *B01J 2540/225* (2013.01); *C07B 2200/07* (2013.01)

(58) Field of Classification Search
CPC .. C07D 401/04; C07D 211/60; C07D 211/78; C07F 15/00; C07F 17/02; B01J 31/24
See application file for complete search history.

(56) References Cited

U.S. PATENT DOCUMENTS

| 5,728,866 A | 3/1998 | Rautenstrauch et al. |
| 6,610,875 B1 | 8/2003 | Lemaire et al. |
| 2002/0055653 A1 | 5/2002 | Driessen-Holscher et al. |
| 2003/0045713 A1 | 3/2003 | Driessen-Holscher et al. |
| 2003/0181736 A1 | 9/2003 | Driessen-Holscher et al. |
| 2003/0187254 A1 | 10/2003 | Perry et al. |
| 2003/0225297 A1 | 12/2003 | Lemaire et al. |
| 2005/0027124 A1 | 2/2005 | Goto et al. |
| 2006/0142310 A1 | 6/2006 | Pfrengle et al. |
| 2007/0161805 A1 | 7/2007 | Goto et al. |
| 2009/0192314 A1 | 7/2009 | Pfrengle et al. |
| 2009/0275750 A1* | 11/2009 | Feng ................. C07D 239/545 540/601 |
| 2010/0105917 A1 | 4/2010 | Mori et al. |
| 2010/0125153 A1 | 5/2010 | Goto et al. |
| 2010/0249428 A1 | 9/2010 | Puentener et al. |
| 2012/0123128 A1 | 5/2012 | Watanabe et al. |
| 2013/0079525 A1 | 3/2013 | Mori et al. |
| 2013/0178485 A1 | 7/2013 | Pfrengle et al. |
| 2013/0184468 A1 | 7/2013 | Puentener et al. |
| 2015/0025089 A1 | 1/2015 | Pfrengle et al. |
| 2015/0025249 A1 | 1/2015 | Puentener et al. |
| 2015/0166481 A1 | 6/2015 | Mori et al. |

FOREIGN PATENT DOCUMENTS

| JP | 09-502459 A | 3/1997 |
| JP | 2002-179692 A | 6/2002 |
| JP | 2002-537305 A | 11/2002 |

(Continued)

OTHER PUBLICATIONS

The practice of Medicinal Chemistry, last volume, Technomics, Inc., (Sep. 25, 1999), pp. 347-365.*
Jonathan Spenner, HeinOnline.*
Anderson et al., Chapter 34 Shio Keisei ni yoru Suiyosei Yuki Kagobutsu no Chosei. Saishin Soyaku Kagaku last volume, Technomics, Inc., Sep. 25, 1999, 347-365.
File Registry on STN, RN 7032-11-3, Ed. Entered STN: Nov. 16, 1984.
File Registry on STN, RN 1010645-58-5, Ed. Entered STN: Mar. 28, 2008.
File Registry on STN, RN 1026661-43-7, Ed. Entered STN: Jun. 8, 2008.
File Registry on STN, RN 1214903-21-5, Ed. Entered STN: Mar. 26, 2010.

(Continued)

Primary Examiner — Alexander R Pagano
Assistant Examiner — Ebenezer O Sackey
(74) Attorney, Agent, or Firm — Foley & Lardner LLP

(57) ABSTRACT

The present invention provides a method of efficiently producing an optically active 6-(3-aminopiperidin-1-yl)-2,4-dioxo-1,2,3,4-tetrahydropyrimidine derivative.
The optically active piperidine-3-carboxamide or a derivative thereof, which is obtained by subjecting 1,4,5,6-tetrahydropyridine-3-carboxamide or a derivative thereof to an asymmetric reduction in the presence of a catalyst, is used as an intermediate.

4 Claims, No Drawings

(56) References Cited

FOREIGN PATENT DOCUMENTS

| | | |
|---|---|---|
| JP | 2003-231691 A | 8/2003 |
| JP | 2009-508873 A | 3/2009 |
| JP | 2011-201908 A | 10/2011 |
| JP | 2012-521385 A | 9/2012 |
| WO | WO 03/072197 A1 | 9/2003 |
| WO | WO 2007/035629 A2 | 3/2007 |
| WO | WO 2008/056259 A2 | 5/2008 |
| WO | WO 2008/102720 A1 | 8/2008 |
| WO | WO 2010/131145 A1 | 11/2010 |
| WO | WO 2011/010579 A1 | 1/2011 |

OTHER PUBLICATIONS

Ichikawa et al., "New Entries in Lewis Acid-Lewis Base Bifunctional Asymmetric Catalyst: Catalytic Enantioselective Reissert Reaction of Pyridine Derivatives," J. Am. Chem. Soc., 2004, 126(38):11808-11809.

Lei et al., "Asymmetric Hydrogenation of Pyridines: Enantioselective Synthesis of Nipecotic Acid Derivatives," Eur. J. Org. Chem., 2006, 19:4343-4347.

Troxler, F., "29. Elektrophile und nucleophile Substitution partiell hydrierter Nicotinsaure-Derivate," Helvetica Chimica Acta, 1973, 56(1):374-389, with English summary on first page.

* cited by examiner

PROCESS FOR PRODUCING HETEROCYCLIC COMPOUND

TECHNICAL FIELD

The present invention relates to a production method of an optically active 6-(3-aminopiperidin-1-yl)-2,4-dioxo-1,2,3,4-tetrahydropyrimidine derivative which is useful as a dipeptidylpeptidase inhibitor, and various intermediates useful therefor, and production methods thereof.

BACKGROUND OF THE INVENTION

An optically active 6-(3-aminopiperidin-1-yl)-2,4-dioxo-1,2,3,4-tetrahydropyrimidine derivative is known to be useful as a dipeptidylpeptidase inhibitor and an agent for the treatment of diabetes.

Patent Document 1 discloses a method of producing a 6-(3-aminopiperidin-1-yl)-2,4-dioxo-1,2,3,4-tetrahydropyrimidine derivative by reacting optically active 3-aminopiperidine with a 6-chloro-2,4-dioxo-1,2,3,4-tetrahydropyrimidine derivative.

Patent Document 2 discloses a method of efficiently producing an optically active 8-(3-aminopiperidin-1-yl)xanthine derivative by subjecting racemic 3-aminopiperidine to acylation with phthalic anhydride, subjecting the obtained 3-phthalimide piperidine to optical resolution with optically active tartaric acid, coupling the obtained optically resolved compound with a xanthine ring, and subjecting the obtained compound to deacylation.

Patent Document 3 discloses a method of optically resolving racemic piperidine-3-carboxamide with optically active lactic acid.

Patent Document 4 discloses a method of producing an optically active piperidine-3-carboxamide derivative by subjecting recemic piperidine-3-carboxamide to stereoselective hydrolysis with an enzyme derived from a microorganism, derivatizing the obtained optically active piperidine-3-carboxamide, and removing optically active nipecotic acid from the mixture.

In addition, the document also discloses a method of producing optically active 3-aminopiperidine by subjecting an optically active piperidine-3-carboxamide derivative to Hofmann rearrangement.

Non-Patent Document 1 discloses a method of producing an optically active nipecotate ester derivative by subjecting a tetrahydropyridinecarboxylate ester derivative to asymmetric reduction with a ruthenium complex.

DOCUMENT LIST

Patent Document

Patent Document 1: WO 2007/035629
Patent Document 2: JP 2011-201908
Patent Document 3: WO 2011/010579
Patent Document 4: WO 2008/102720

Non-Patent Document

Non-Patent Document 1: Eur. J. Org. Chem. 2006, p. 4343-4347.

SUMMARY OF THE INVENTION

Problems to be Solved by the Invention

The aim of the present invention is to provide a method of efficiently producing an optically active 6-(3-aminopiperidin-1-yl)-2,4-dioxo-1,2,3,4-tetrahydropyrimidine derivative using a relatively inexpensive raw material compound.

The other aim of the present invention is to provide various intermediates useful for producing an optically active 6-(3-aminopiperidin-1-yl)-2,4-dioxo-1,2,3,4-tetrahydropyrimidine derivative, and production methods thereof.

Means of Solving the Problems

The present inventors have conducted intensive studies to solve the above-mentioned problems, and have found that optically active piperidine-3-carboxamide or a derivative thereof can be efficiently obtained by subjecting 1,4,5,6-tetrahydropyridine-3-carboxamide or a derivative thereof to an asymmetric reduction in the presence of a catalyst, and an optically active 6-(3-aminopiperidin-1-yl)-2,4-dioxo-1,2,3,4-tetrahydropyrimidine derivative can be efficiently produced from the obtained compound as an intermediate, and completed the present invention based on these findings.

Accordingly, the present invention provides the following.

[1] A method of producing an optically active form of a compound represented by the formula:

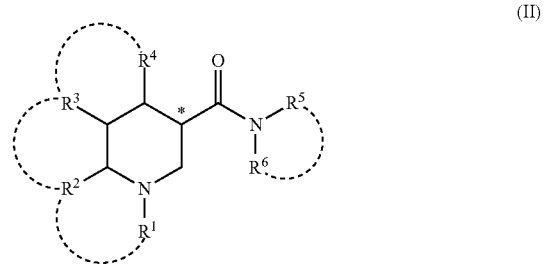

wherein
$R^1$ is a hydrogen atom, an optionally substituted hydrocarbon group, an optionally substituted heterocyclic group, or a protecting group;
$R^2$, $R^3$ and $R^4$ are independently a hydrogen atom or a substituent;
$R^5$ and $R^6$ are independently a hydrogen atom, an optionally substituted hydrocarbon group, or an optionally substituted heterocyclic group; or
$R^1$ and $R^2$ in combination, $R^2$ and $R^3$ in combination, $R^3$ and $R^4$ in combination, or $R^5$ and $R^6$ in combination optionally form a 5- to 8-membered ring together with the adjacent atoms, and the carbon atom marked with * is an asymmetric carbon atom, or a salt thereof, which comprises subjecting a compound represented by the formula:

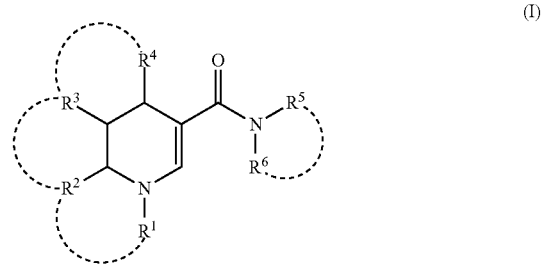

wherein each symbol is as defined above, or a salt thereof, to a hydrogenation reaction in the presence of an organic metal complex.

[2] The method according to the above-mentioned [1], wherein the organic metal complex is a transition metal complex.

[3] The method according to the above-mentioned [2], wherein the transition metal complex is a ruthenium complex.

[4] The method according to the above-mentioned [3], wherein the ruthenium complex is represented by the formula:

(VIII)

wherein $R^a$ is an optionally substituted $C_{1-3}$ alkyl group; and $L^a$ is a diphosphine ligand.

[5] The method according to the above-mentioned [1], wherein the hydrogenation reaction is performed in the presence of an alkali metal halide or a compound represented by the formula:

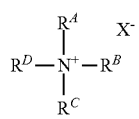

(VI)

wherein $R^A$, $R^B$, $R^C$ and $R^D$ are independently a hydrogen atom, or an optionally substituted hydrocarbon group; and X is a halogen atom.

[6] A compound represented by the formula:

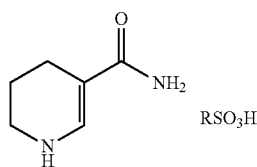

(XII)

wherein R is an optionally substituted hydrocarbon group.

[7] An optically active form of a compound represented by the formula:

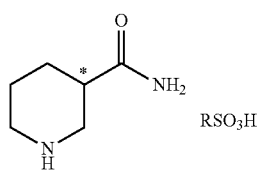

(XIII)

wherein

R is an optionally substituted hydrocarbon group, and the carbon atom marked with * is an asymmetric carbon atom.

[8] A method of producing an optically active form of a compound represented by the formula:

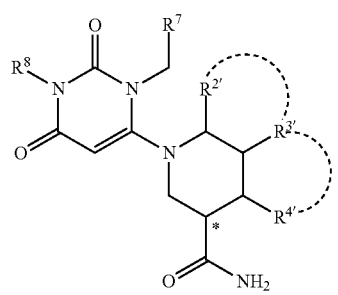

(IV)

wherein $R^{2'}$, $R^{3'}$ and $R^{4'}$ are independently a hydrogen atom, an optionally substituted hydrocarbon group, or an optionally substituted heterocyclic group; or $R^{2'}$ and $R^{3'}$ in combination, or $R^{3'}$ and $R^{4'}$ in combination optionally form a 5- to 8-membered ring together with the adjacent atoms;

$R^7$ and $R^8$ are independently an optionally substituted hydrocarbon group, a hydrogen atom, or an optionally substituted heterocyclic group; and the carbon atom marked with * is an asymmetric carbon atom, or a salt thereof, which comprises reacting an optically active form of a compound represented by the formula:

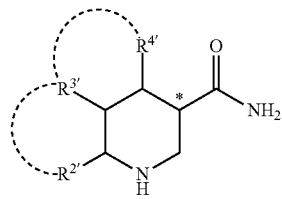

(II')

wherein each symbol is as defined above, or a salt thereof, with a compound represented by the formula:

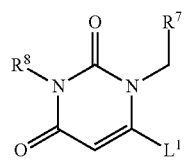

(III)

wherein $L^1$ is a leaving group, and the other symbols are as defined above, or a salt thereof.

[9] A method of producing an optically active form of a compound represented by the formula:

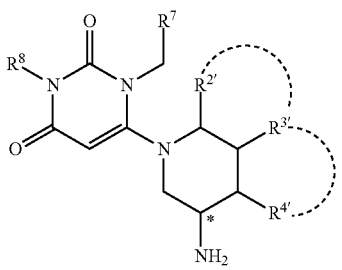

(V)

wherein

R[2'], R[3'] and R[4'] are independently a hydrogen atom, an optionally substituted hydrocarbon group, or an optionally substituted heterocyclic group, or R[2'] and R[3'] in combination, or R[3'] and R[4'] in combination optionally form a 5- to 8-membered ring together with the adjacent atoms;

R[7] and R[8] are independently an optionally substituted hydrocarbon group, a hydrogen atom, or an optionally substituted heterocyclic group; and the carbon atom marked with * is an asymmetric carbon atom, or a salt thereof, which comprises subjecting an optically active form of a compound represented by the formula:

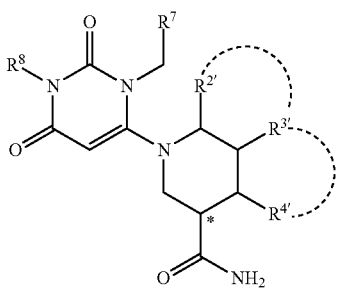

(IV)

wherein each symbol is as defined above,
or a salt thereof, to a rearrangement reaction.

[10] The method according to the above-mentioned [9], which further comprises (1) a step of subjecting a compound represented by the formula:

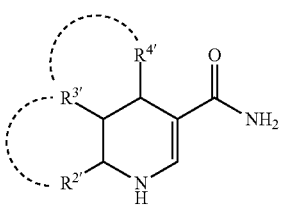

(I')

wherein each symbol is as defined in the above-mentioned [9], or a salt thereof, to a hydrogenation reaction in the presence of an organic metal complex to give an optically active form of a compound represented by the formula:

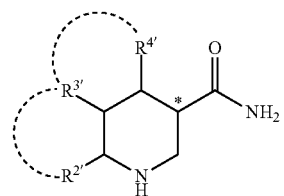

(II')

wherein each symbol is as defined in the above-mentioned [9], or a salt thereof; and (2) a step of reacting an optically active form of a compound represented by the formula:

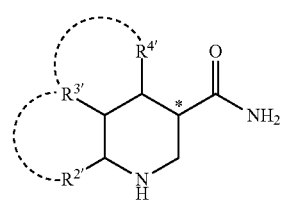

(II')

wherein each symbol is as defined above,
or a salt thereof, with a compound represented by the formula:

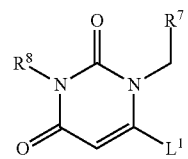

(III)

wherein

L[1] is a leaving group; and the other symbols are as defined in the above-mentioned [9], or a salt thereof to give an optically active form of a compound represented by the formula:

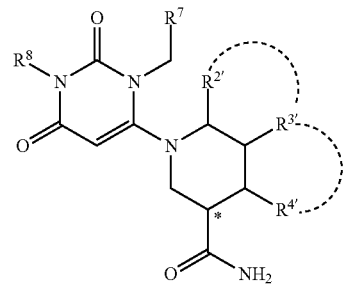

(IV)

wherein each symbol is as defined above,
or a salt thereof.

[11] A ruthenium complex represented by the formula:

[Ru(OCOR[a1])$_2$L[a1]]   (VIII')

wherein

R[a1] is a trifluoromethyl group; and

L[a1] is an optically active diphosphine ligand selected from
(1) an optically active form consisting of a compound represented by the formula:

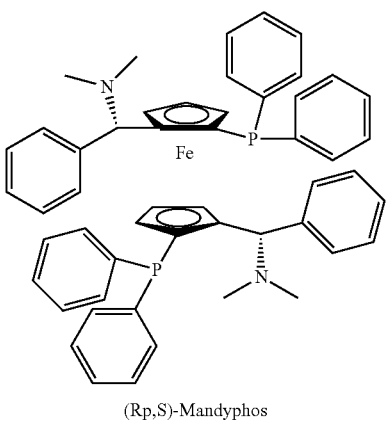

(Rp,S)-Mandyphos or
the formula:

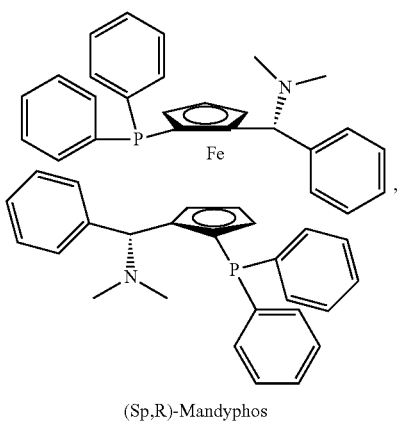

(Sp,R)-Mandyphos or
a mixture thereof, and
(2) an optically active form of a compound represented by the formula:

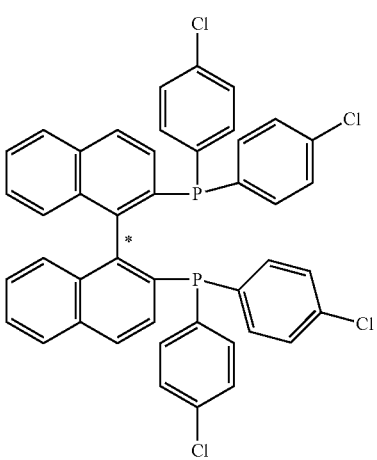

wherein the bond marked with * is a chiral axis.

Effect of the Invention

According to the present invention, an optically active 6-(3-aminopiperidin-1-yl)-2,4-dioxo-1,2,3,4-tetrahydropyrimidine derivative can be efficiently produced with high purity in high yield.

The derivative is useful as a dipeptidylpeptidase inhibitor and an agent for the treatment of diabetes.

In addition, according to the present invention, various intermediates for producing an optically active 6-(3-aminopiperidin-1-yl)-2,4-dioxo-1,2,3,4-tetrahydropyrimidine derivative, and efficient production methods thereof can be provided.

Moreover, according to the present invention, a ruthenium complex useful for a hydrogenation reaction can be provided.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, triflubroacetyl, trichioroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-16}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkyl-sulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),

(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, triazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazolyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N- methylamino) and a ($C_{1-6}$ alkyl)($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbathoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

The definition of each symbol and compounds in the formulas (I) and (II) are explained in detail in the following.

$R^1$ is a hydrogen atom, an optionally substituted hydrocarbon group, an optionally substituted heterocyclic group, or a protecting group.

Preferable examples of the "hydrocarbon group" of the "optionally substituted hydrocarbon group" represented by $R^1$ include a $C_{1-6}$ alkyl group, a $C_{3-10}$ cycloalkyl group, a $C_{6-14}$ aryl group, a $C_{7-16}$ aralkyl group and the like.

Preferable examples of the "heterocyclic group" of the "optionally substituted heterocyclic group" represented by $R^1$ include (i) an aromatic heterocyclic group and (ii) a non-aromatic heterocyclic group, each containing 1 to 4 heteroatoms selected from a nitrogen atom, a sulfur atom and an oxygen atom, as a ring-constituting atom besides carbon atom.

The "protecting group" represented by $R^1$ is an amino-protecting group known per se, and preferable examples thereof include amide type protecting groups such as a formyl group, an acetyl group, a benzoyl group and the like; and carbamate type protecting groups such as a 9-fluorenylmethoxycarbonyl group, a tert-butoxycarbonyl group, a benzyloxycarbonyl group and the like. The amino-protecting groups and the like described in Green et al., Protective Groups in Organic Synthesis, 3rd Edition, 1998, John Wiley & Sons, Inc., can be referred to for these protecting group.

$R^1$ is preferably a hydrogen atom.

$R^2$, $R^3$ and $R^4$ are independently a hydrogen atom or a substituent.

Preferable examples of the "substituent" represented by $R^2$, $R^3$ or $R^4$ include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted hydroxy group, an optionally substituted silyl group and the like. Among them, an optionally substituted hydrocarbon group, and an optionally substituted heterocyclic group are more preferable.

$R^2$, $R^3$ and $R^4$ is preferably independently a hydrogen atom, a halogen atom, a cyano group, a nitro group, an optionally substituted hydrocarbon group, an optionally substituted heterocyclic group, an acyl group, an optionally substituted amino group, an optionally substituted carbamoyl group, an optionally substituted hydroxy group, or an optionally substituted silyl group; more preferably independently a hydrogen atom, an optionally substituted hydrocarbon group, or an optionally substituted heterocyclic group; particularly preferably a hydrogen atom.

$R^5$ and $R^6$ are independently a hydrogen atom, an optionally substituted hydrocarbon group, or an optionally substituted heterocyclic group.

Preferable examples of the "hydrocarbon group" of the "optionally substituted hydrocarbon group" represented by $R^5$ or $R^6$ include a $C_{1-6}$ alkyl group, a $C_{3-10}$ cycloalkyl group, a $C_{6-14}$ aryl group, a $C_{7-16}$ aralkyl group and the like.

Preferable examples of the "heterocyclic group" of the "optionally substituted heterocyclic group" represented by $R^5$ or $R^6$ include (i) an aromatic heterocyclic group and (ii) a non-aromatic heterocyclic group, each containing 1 to 4 heteroatoms selected from a nitrogen atom, a sulfur atom and an oxygen atom, as a ring-constituting atom besides carbon atom.

$R^5$ and $R^6$ are preferably hydrogen atoms.

Alternatively, $R^1$ and $R^2$ in combination, $R^2$ and $R^3$ in combination, $R^3$ and $R^4$ in combination, or $R^5$ and $R^6$ in combination optionally form a 5- to 8-membered ring together with the adjacent atoms.

Preferable examples of the "5- to 8-membered ring" formed by $R^2$ and $R^3$ in combination, or $R^3$ and $R^4$ in combination include a $C_{5-8}$ cycloalkane ring, a $C_{5-8}$ cycloalkene ring, a 5- to 8-membered monocyclic non-aromatic heterocycle and the like.

Examples of the "$C_{5-8}$ cycloalkane ring" exemplified as the above-mentioned "5- to 8-membered ring" include rings such as cyclopentane, cyclohexane, cycloheptane, cyclooctane and the like.

Examples of the "$C_{5-8}$ cycloalkene ring" exemplified as the above-mentioned "5- to 8-membered ring" include rings such as cyclopentene, cyclohexene, cycloheptene, cyclooctene and the like.

Examples of the "5- to 8-membered monocyclic non-aromatic heterocycle" exemplified as the above-mentioned "5- to 8-membered ring" include a 5- to 8-membered monocyclic non-aromatic heterocycle containing heteroatom(s) selected from a nitrogen atom, a sulfur atom and an oxygen atom, as a ring-constituting atom besides carbon atom, and specific examples thereof include rings such as tetrahydrothiophene, tetrahydrofuran, pyrroline, pyrrolidine, imidazoline, imidazolidine, oxazoline, oxazolidine, pyrazoline, pyrazolidine, thiazoline, thiazolidine, isoxazoline, isothiazoline, tetrahydroisothiazole (isothiazolidine), tetrahydroisoxazole (isoxazolidine), piperidine, piperazine, tetrahydropyridine, dihydropyridine, dihydrothiopyran, tetrahydropyrimidine, dihydropyrimidine, tetrahydropyridazine, dihydropyridazine, dihydropyran, tetrahydropyran, tetrahydrothiopyran, morpholine, thiomorpholine, azepane, diazepane, azepine, oxepane, azocane, diazocane and the like.

Preferable examples of the "5- to 8-membered ring" formed by $R^1$ and $R^2$ in combination, or $R^5$ and $R^6$ in combination together with the adjacent atoms include a 5- to 8-membered monocyclic nitrogen-containing non-aromatic heterocycle and the like.

Examples of the "5- to 8-membered monocyclic nitrogen-containing non-aromatic heterocycle" exemplified as the above-mentioned "5- to 8-membered ring" include a 5- to 8-membered monocyclic non-aromatic heterocycle containing at least one nitrogen atom and optionally containing heteroatom(s) selected from a sulfur atom and an oxygen atom, as a ring-constituting atom besides carbon atom, and specific examples thereof include rings such as pyrroline, pyrrolidine, imidazoline, imidazolidine, oxazoline, oxazolidine, pyrazoline, pyrazolidine, thiazoline, thiazolidine, isoxazoline, isothiazoline, tetrahydroisothiazole (isothiazolidine), tetrahydroisoxazole (isoxazolidine), piperidine, piperazine, tetrahydropyridine, dihydropyridine, tetrahydropyrimidine, dihydropyrimidine, tetrahydropyridazine, dihydropyridazine, morpholine, thiomorpholine, azepane, diazepane, azocane, diazocane and the like.

In preferable embodiment,
the compound represented by the formula (I) is a compound represented by the formula:

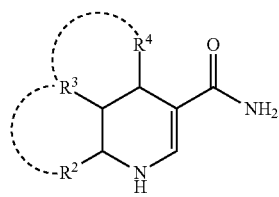
(Ia)

wherein each symbol is as defined above; and
the compound represented by the formula (II) is a compound represented by the formula:

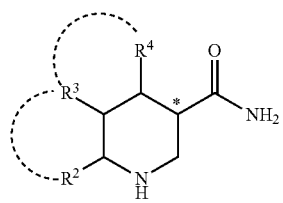
(IIa)

wherein each symbol is as defined above.

In more preferable embodiment,
the compound represented by the formula (I) is a compound represented by the formula (I'); and
the compound represented by the formula (II) is a compound represented by the formula (II').

In further more preferable embodiment,
the compound represented by the formula (I) is 1,4,5,6-tetrahydropyridine-3-carboxamide; and
the compound represented by the formula (II) is piperidine-3-carboxamide.

The compounds represented by the formulas (I) and (II) may be each a salt.

Examples of the salts of the compounds represented by the formula formulas (I) and (II) include metal salts, ammonium salts, salts with an organic base, salts with an inorganic acid, salts with an organic acid, salts with a basic or acidic amino acid, and the like.

Preferable examples of the metal salt include alkaline metal salts such as sodium salt, potassium salt and the like; alkaline earth metal salts such as calcium salt, magnesium salt, barium salt and the like; aluminum salt, and the like.

Preferable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine or the like.

Preferable examples of the salt with an inorganic acid include salts with hydrofluoric acid, hydrochloric acid, hydrobromic acid, hydroiodic acid, nitric acid, sulfuric acid, sulfurous acid, phosphoric acid, phosphorous acid, carbonic acid, bicarbonic acid or the like.

Preferable examples of the salt with an organic acid include salts with a carboxylic acid (i.e., an organic compound having one or more carboxy groups; specific examples thereof include formic acid, acetic acid, benzoic acid, trifluoroacetic acid, phthalic acid, fumaric acid, oxalic acid, tartaric acid, maleic acid, citric acid, succinic acid, malic acid or the like); or a sulfonic acid (i.e., an organic compound having one or more sulfo groups; specific examples thereof include methanesulfonic acid, trifluoromethanesulfonic acid, benzenesulfonic acid, p-toluenesulfonic acid, camphorsulfonic acid or the like).

Preferable examples of the salt with a basic amino acid include salts with arginine, lysine, ornithine or the like. Preferable examples of the salt with an acidic amino acid include salts with aspartic acid, glutamic acid or the like.

The salts of the compounds represented by the formula (I) and (II) are each preferably a salt with an organic acid, or a salt with an inorganic acid; more preferably a sulfonate or a salt with sulfuric acid; still more preferably a sulfonate.

The sulfonate means a salt with an organic compound having one or more sulfo groups, preferably a salt with a compound represented by the formula:

$R^b SO_3 H$ (VII)

wherein $R^b$ is an optionally substituted hydrocarbon group.

In the above-mentioned formula (VII), preferable examples of the "hydrocarbon group" of the "optionally substituted hydrocarbon group" represented by $R^b$ include a $C_{1-6}$ alkyl group, a $C_{3-10}$ cycloalkyl group, a $C_{6-14}$ aryl group, a $C_{7-16}$ aralkyl group and the like. Among them, a $C_{1-6}$ alkyl group and a $C_{6-14}$ aryl group are preferable, and a $C_{6-14}$ aryl group is more preferable.

In the above-mentioned formula (VII), $R^b$ is preferably an optionally substituted $C_{6-14}$ aryl group; more preferably an optionally substituted phenyl group; further more preferably a phenyl group optionally substituted by $C_{1-6}$ alkyl group(s); particularly preferably a phenyl group optionally substituted by methyl.

The above-mentioned compound represented by the formula (VII) is specifically preferably methanesulfonic acid, trifluoromethanesulfonic acid, benzenesulfonic acid or p-toluenesulfonic acid, more preferably p-toluenesulfonic acid.

The compound represented by the formula (I) or a salt thereof is preferably a salt of 1,4,5,6-tetrahydropyridine-3-carboxamide with sulfonic acid. In addition, the optically active form of the compound represented by the formula (II) or a salt thereof is preferably a salt of optically active piperidine-3-carboxamide with sulfonic acid.

The compound represented by the formula (I) or a salt thereof is particularly preferably 1,4,5,6-tetrahydropyridine-3-carboxamide p-toluenesulfonate. In addition, the optically active form of the compound represented by the formula (II) or a salt thereof is particularly preferably optically active piperidine-3-carboxamide p-toluenesulfonate.

The compounds represented by the formulas (I) and (II) may be each a solvate (e.g., a hydrate, an ethanolate, etc.) or a non-solvate (e.g., a non-hydrate, etc.), and both are encompassed in compounds (I) or (II).

A compound labeled with an isotope and the like is also encompassed in the compounds represented by the formulas (I) and (II).

A deuterium conversion form wherein $^1H$ is converted to $^2H(D)$ is also encompassed in the compounds represented by the formulas (I) and (II).

The definition of each symbol and compounds in the formula (I'), formula (II'), formula (III), formula (IV), formula (V), formula (XII) and formula (XIII) are explained in detail in the following.

R is an optionally substituted hydrocarbon group.

Preferable examples of the "hydrocarbon group" of the "optionally substituted hydrocarbon group" represented by R include a $C_{1-6}$ alkyl group, a $C_{3-10}$ cycloalkyl group, a $C_{6-14}$ aryl group, a $C_{7-16}$ aralkyl group and the like. Among them, a $C_{1-6}$ alkyl group and a $C_{6-14}$ aryl group are preferable, and a $C_{6-14}$ aryl group is more preferable.

R is preferably an optionally substituted $C_{6-14}$ aryl group; more preferably an optionally substituted phenyl group; further more preferably a phenyl group optionally substituted by $C_{1-6}$ alkyl group(s).

R is particularly preferably a phenyl group optionally substituted by methyl.

In preferable embodiment of formula (XII), the compound represented by the formula (XII) is a compound represented by the following formula:

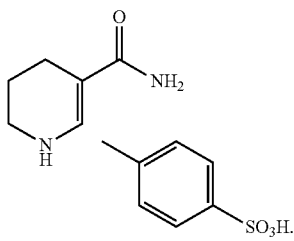

(XII')

In preferable embodiment of formula (XIII), the compound represented by the formula (XIII) is a compound represented by the following formula:

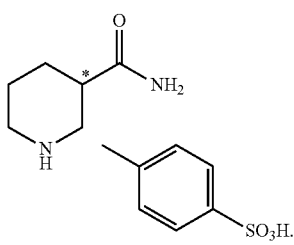

(XIII')

$R^{2'}$, $R^{3'}$ and $R^{4'}$ are independently a hydrogen atom, an optionally substituted hydrocarbon group, or an optionally substituted heterocyclic group.

$R^{2'}$, $R^{3'}$ and $R^{4'}$ are preferably hydrogen atoms.

Alternatively, $R^{2'}$ and $R^{3'}$ in combination, or $R^{3'}$ and $R^{4'}$ in combination optionally form a 5- to 8-membered ring together with the adjacent atoms.

Preferable examples of the "5- to 8-membered ring" formed by $R^{2'}$ and $R^{3'}$ in combination, or $R^{3'}$ and $R^{4'}$ in combination include those similar to the preferable "5- to 8-membered ring" formed by $R^2$ and $R^3$ in combination, or $R^3$ and $R^4$ in combination.

$R^7$ and $R^8$ are independently an optionally substituted hydrocarbon group, a hydrogen atom, or an optionally substituted heterocyclic group.

Preferable examples of the "hydrocarbon group" of the "optionally substituted hydrocarbon group" represented by $R^7$ include a $C_{6-14}$ aryl group.

Preferable examples of the "heterocyclic group" of the "optionally substituted heterocyclic group" represented by $R^7$ include an aromatic heterocyclic group containing 1 to 4 heteroatoms selected from a nitrogen atom, a sulfur atom and an oxygen atom, as a ring-constituting atom besides carbon atom.

The "hydrocarbon group" of the "optionally substituted hydrocarbon group" represented by $R^7$ and the "heterocyclic group" of the "optionally substituted heterocyclic group" represented by $R^7$ each optionally has 1 to 5 (preferably 1 to 3) substituents at substitutable position(s). Examples of the substituent include the above-mentioned Substituent Group A. The substituent is preferably a halogen atom, more preferably a fluorine atom.

$R^7$ is preferably an optionally substituted $C_{6-14}$ aryl group; more preferably an optionally substituted phenyl group; further more preferably a phenyl group optionally substituted by 1 to 3 substituents selected from a halogen atom (e.g., a fluorine atom) and a cyano group.

Preferable examples of $R^7$ include a phenyl group substituted by cyano group(s), and a phenyl group substituted by cyano group(s) and fluorine atom(s). Among them, a phenyl group substituted by cyano group(s) is preferable.

Preferable examples of the "hydrocarbon group" of the "optionally substituted hydrocarbon group" represented by $R^8$ include a $C_{1-6}$ alkyl group.

$R^8$ is preferably a hydrogen atom or a $C_{1-6}$ alkyl group; more preferably a $C_{1-6}$ alkyl group; further more preferably a methyl group.

$L^1$ is a leaving group.

Examples of the leaving group represented by $L^1$ include a halogen atom; optionally halogenated $C_{1-6}$ alkylsulfonyloxy groups such as methanesulfonyloxy, ethanesulfonyloxy, trichloromethanesulfonyloxy, trifluoromethanesulfonyloxy and the like; $C_{6-10}$ arylsulfonyloxy groups optionally having substituent(s) such as phenylsulfonyloxy, m-nitrophenylsulfonyloxy, p-toluenesulfonyloxy, naphthylsulfonyloxy and the like (for example, $C_{6-10}$ arylsulfonyloxy groups optionally having 1 to 3 substituents selected from a $C_{1-6}$ alkyl group, a $C_{1-6}$ alkoxy group and a nitro group); acyloxy groups such as trichloroacetoxy, trifluoroacetoxy and the like, and the like.

The leaving group represented by $L^1$ is preferably a halogen atom, particularly preferably a chlorine atom.

In preferable embodiment, the compound represented by the formula (I') is 1,4,5,6-tetrahydropyridine-3-carboxamide;

the compound represented by the formula (II') is piperidine-3-carboxamide;

the compound represented by the formula (IV) is a compound represented by the formula:

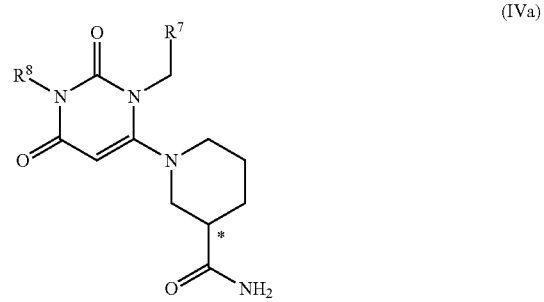

(IVa)

wherein each symbol is as defined above; and the compound represented by the formula (V) is a compound represented by the formula:

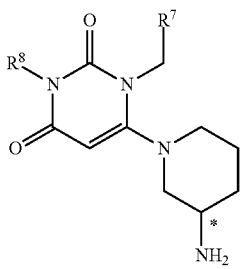

(Va)

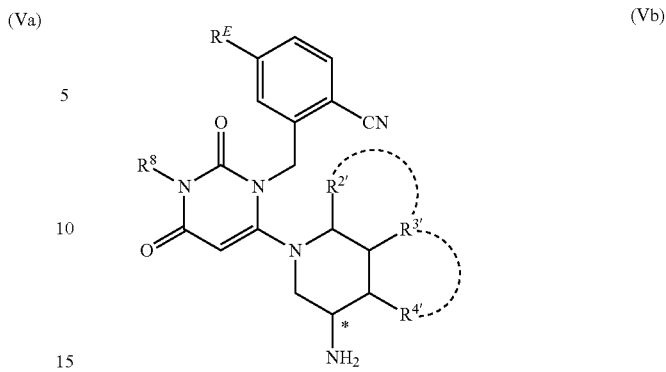

(Vb)

wherein each symbol is as defined above.

In another preferable embodiment, the compound represented by the formula (III) is a compound represented by the formula:

wherein each symbol is as defined above.

In more preferable embodiment, the compound represented by the formula (I') is 1,4,5,6-tetrahydropyridine-3-carboxamide;

the compound represented by the formula (II') is piperidine-3-carboxamide;

the compound represented by the formula (III) is a compound represented by the formula:

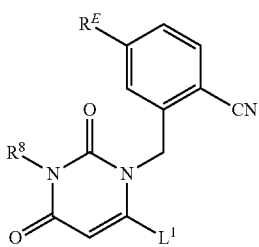

(IIIb)

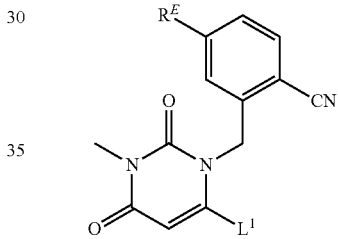

(IIIc)

wherein $R^E$ is a hydrogen atom or a fluorine atom; and $R^8$ and $L^1$ are each as defined above;

the compound represented by the formula (IV) is a compound represented by the formula:

wherein each symbol is as defined above;

the compound represented by the formula (IV) is a compound represented by the formula:

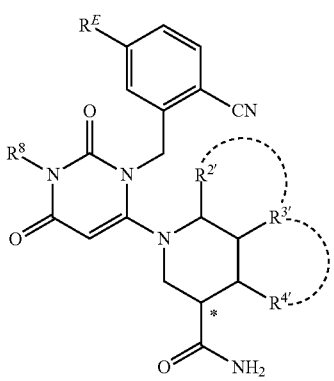

(IVb)

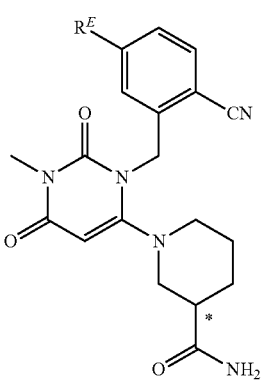

(IVc)

wherein each symbol is as defined above; and the compound represented by the formula (V) is a compound represented by the formula:

wherein each symbol is as defined above; and the compound represented by the formula (V) is a compound represented by the formula:

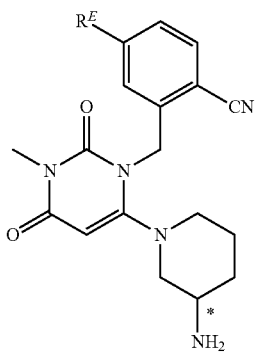

(Vc)

wherein each symbol is as defined above.

R^E is particularly preferably a hydrogen atom.

The compounds represented by the formulas (I') and (II') are preferably each a salt.

Examples of the salts of the compounds represented by the formulas (I') and (II') include those similar to the salts of the compounds represented by the formulas (I) and (II), and preferable examples of the "salt" include those similar to the preferable salts of the compounds represented by the formulas (I) and (II).

The compound represented by the formula (I') or a salt thereof is preferably a salt of 1,4,5,6-tetrahydropyridine-3-carboxamide with sulfonic acid. In addition, the optically active form of the compound represented by the formula (II') or a salt thereof is preferably a salt of optically active piperidine-3-carboxamide with sulfonic acid.

The compound represented by the formula (I') or a salt thereof is particularly preferably 1,4,5,6-tetrahydropyridine-3-carboxamide p-toluenesulfonate. In addition, the optically active form of the compound represented by the formula (II') or a salt thereof is particularly preferably optically active piperidine-3-carboxamide p-toluenesulfonate.

Examples of the salt of the compound represented by the formulas (III), (IV) and (V) include those similar to the salts of the compounds represented by the formulas (I) and (II).

The compounds represented by the formulas (I'), (II'), (III), (IV) and (V) may be each a solvate (e.g., a hydrate, an ethanolate, etc.) or a non-solvate (e.g., non-hydrate, etc.), and both are encompassed in the compounds represented by the formulas (I'), (II'), (III), (IV) and (V).

A compound labeled with isotope and the like is also encompassed in the compounds represented by the formulas (I'), (II'), (III), (IV) and (V).

A deuterium conversion form wherein $^1H$ is converted to $^2H(D)$ is also encompassed in the compounds represented by the formulas (I'), (II'), (III), (IV) and (V).

The production method of the optically active form of the piperidine-3-carboxamide or a derivative thereof (the compound represented by the formula (II)) or a salt thereof (Production Method (A)), and the production method of the optically active form of the 6-(3-aminopiperidin-1-yl)-2,4-dioxo-1,2,3,4-tetrahydropyrimidine derivative (the compound represented by the formula (V)) or a salt thereof using the above-mentioned compound (Production Method (B)) are explained in detail below.

[Production Method (A)]

The optically active form of the compound represented by the formula (II) or a salt thereof can be produced according to Production Method (A) shown in the following reaction scheme.

Reaction Scheme

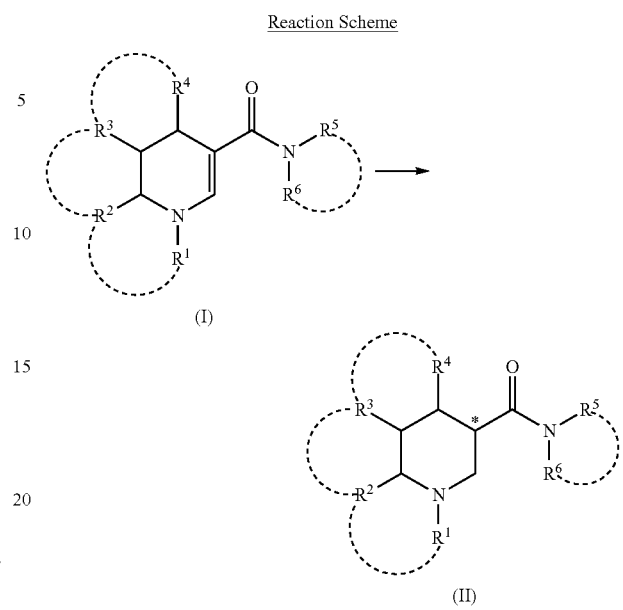

wherein each symbol is as defined above.

The reagents and conditions used for Production Method (A) are explained in detail below.

Production Method (A) is a method of producing the optically active form of the compound represented by the formula (II) or a salt thereof by subjecting the compound represented by the formula (I) or a salt thereof to a hydrogenation reaction in the presence of an organic metal complex.

Examples of the "organic metal complex" include typical metal complexes such as boron complexes, aluminium complexes, gallium complexes and the like, in addition to "transition metal complexes (organic transition metal complexes)".

Preferable examples of the "organic metal complex" include "transition metal complexes (organic transition metal complexes)".

Examples of the "transition metal complex" include compounds capable of catalyzing an asymmetric hydrogenation reaction, wherein the "transition metal" is coordinated with a "ligand" (preferably an optically active "ligand"). Examples of the optically active "ligand" include phosphine ligands, diphosphine ligands, amine ligands, diamine ligands, phosphine amine ligands and the like. The "transition metal" is, for example, 0 to 6 valent, preferably 0 to 4 valent, particularly preferably 0 to 3 valent.

Preferable examples of "transition metal complex" include rhodium complexes, ruthenium complexes, iridium complexes, palladium complexes, nickel complexes, copper complexes, osmium complexes, platinum complexes, iron complexes, gold complexes, silver complexes, zinc complexes, titanium complexes, cobalt complexes, zirconium complexes, samarium complexes and the like; more preferred are rhodium complexes, ruthenium complexes, iridium complexes, palladium complexes, nickel complexes and copper complexes; further more preferred are rhodium complexes, ruthenium complexes and iridium complexes; and particularly preferred are ruthenium complexes.

Among the "transition metal complexes", specific examples of the rhodium complex, ruthenium complex, iridium complex, palladium complex, nickel complex and copper complex are shown below (in the following transition metal complex, L is a diphosphine ligand, Ar is benzene optionally having substituent(s) (the substituent is preferably a $C_{1-6}$ alkyl group), Cp* is pentamethylcyclopentadienyl, Cp is cyclopentadienyl, cod is 1,5-cyclooctadiene, Tf is trifluoromethanesulfonyl, nbd is norbornadiene, Ph is phenyl, Ac is acetyl, Et is ethyl, dmf is N,N-dimethylformamide, 2-methylallyl is $\eta^3$-2-methylallyl, en is ethylenediamine, dpen is 1,2-diphenylethylenediamine, daipen is 1,1-di(4-anisyl)-2-isopropyl-1,2-ethylenediamine, and n is an integer of 1 or more. 1,2-Diphenylethylenediamine and 1,1-di(4-anisyl)-2-isopropyl-1,2-ethylenediamine are each (R)-form, (S)-form, or a mixture of (R)-form and (S)-form (the ratio is not limited), preferably an optically active form).

rhodium complexes: [RhCl(L)]$_2$, [RhEr(L)]$_2$, [RhI(L)]$_2$, [RhCp*(L)]$_2$, [Rh(cod)(L)]OTf, [Rh(cod)(L)]BF$_4$, [Rh(cod)(L)]ClO$_4$, [Rh(cod)(L)]PF$_6$, [Rh(cod)(L)]SbF$_6$, [Rh(cod)(L)]BPh$_4$, [Rh(cod)(L)]B$\{3,5$-$(CF_3)_2C_6H_3\}_4$, [Rh(nbd)(L)]OTf, [Rh(nbd)(L)]BF$_4$, [Rh(nbd)(L)]ClO$_4$, [Rh(nbd)(L)]PF$_6$, [Rh(nbd)(L)]SbF$_6$, [Rh(nbd)(L)]BPh$_4$, [Rh(nbd)(L)]B$\{3,5$-$(CF_3)_2C_6H_3\}_4$, [Rh(L)(CH$_3$OH)$_2$]OTf, [Rh(L)(CH$_3$OH)$_2$]BF$_4$, [Rh(L)(CH$_3$OH)$_2$]ClO$_4$, [Rh(L)(CH$_3$OH)$_2$]PF$_6$, [Rh(L)(CH$_3$OH)$_2$]EPh$_4$;

ruthenium complexes: [RuCl$_2$(L)]$_n$, [RuBr$_2$(L)]$_n$, [RuI$_2$(L)]$_n$, [Ru(OAc)$_2$(L)], [Ru(OCOCF$_3$)$_2$(L)], (NH$_2$Me$_2$)[{RuCl(L)}$_2$(μ-Cl)$_3$], (NH$_2$Et$_2$)[{RuCl(L)}$_2$(μ-Cl)$_3$], (NH$_2$Me$_2$)[{RuBr(L)}$_2$ (μ-Br)$_3$], (NH$_2$Et$_2$)[{RuBr(L)}$_2$ (μ-Br)$_3$], (NH$_2$Me$_2$)[{RuI(L)}$_2$ (μ-I)$_3$], (NH$_2$Et$_2$)[{RuI(L)}$_2$ (μ-I)$_3$], [Ru$_2$Cl$_4$(L)$_2$(NEt$_3$)], [RuCl$_2$(L)(dmf)$_n$], [Ru(2-methylallyl)$_2$ (L)], [RuCl(Ar)(L)]Cl, [RuCl(Ar)(L)]Br, [RuCl(Ar)(L)]I, [RuCl(Ar)(L)]OTf, [RuCl(Ar)(L)]ClO$_4$, [RuCl(Ar)(L)]PF$_6$, [RuCl(Ar)(L)]BF$_4$, [RuCl(Ar)(L)]BPh$_4$, [RuBr(Ar)(L)]Cl, [RuBr(Ar)(L)]Br, [RuBr(Ar)(L)]I, [RuI(Ar)(L)]Cl, [RuI(Ar)(L)]Br, [RuI(Ar)(L)]I, [Ru(L)](OTf)$_2$, [Ru(L)](BF$_4$)$_2$, [Ru(L)](ClO$_4$)$_2$, [Ru(L)](PF$_6$)$_2$, [Ru(L)](BPh$_4$)$_2$, [RuH(L)$_2$]Cl, [RuH(L)$_2$]OTf, [RuH(L)$_2$]BF$_4$, [RuH(L)$_2$]ClO$_4$, [RuH(L)$_2$]PF$_6$, [RuH(L)$_2$]BPh$_4$, [RuH(CH$_3$CN)(L)]Cl, [RuH(CH$_3$CN)(L)]OTf, [RuH(CH$_3$CN)(L)]BF$_4$, [RuH(CH$_3$CN)(L)]ClO$_4$, [RuH(CH$_3$CN)(L)]PF$_6$, [RuH(CH$_3$CN)(L)]BPh$_4$, [RuCl(L)]OTf, [RuCl(L)]BF$_4$, [RuCl(L)]ClO$_4$, [RuCl(L)]PF$_6$, [RuCl(L)]BPh$_4$, [RuBr(L)]OTf, [RuBr(L)]BF$_4$, [RuBr(L)]ClO$_4$, [RuBr(L)]PF$_6$, [RuBr(L)]BPh$_4$, [RuI(L)]OTf, [RuI(L)]BF$_4$, [RuI(L)]ClO$_4$, [RuI(L)]PF$_6$, [RuI(L)]BPh$_4$, [RuCl$_2$ (L)(en)], [RuCl$_2$ (L)(dpen)], [RuCl$_2$ (L)(daipen)], [RuH($\eta^1$-BH$_4$)(L)(en)], [RuH($\eta^1$-BH$_4$)(L)(daipen)], [RuH($\eta^1$-BH$_4$)(L)(dpen)] (in the above-mentioned [RuCl$_2$(L)(en)], [RuCl$_2$(L)(dpen)] and [RuCl$_2$(L)(daipen)], instead of en, dpen and daipen which are the diamine ligands, the diamine ligands such as 1,2-cyclohexanediamine, 1,2-cycloheptanediamine, 2,3-dimethylbutanediamine, 1-methyl-2,2-diphenyl-1,2-ethylenediamine, 1-isobutyl-2,2-diphenyl-1,2-ethylenediamine, 1-isopropyl-2,2-diphenyl-1,2-ethylenediamine, 1,1-di(4-anisyl)-2-methyl-1,2-ethylenediamine, 1,1-di(4-anisyl)-2-isobutyl-1,2-ethylenediamine, 1,1-di(4-anisyl)-2-benzyl-1,2-ethylenediamine, 1-methyl-2,2-dinaphthyl-1,2-ethylenediamine, 1-isobutyl-2,2-dinaphthyl-1,2-ethylenediamine, 1-isopropyl-2,2-dinaphthyl-1,2-ethylenediamine, propanediamine, butanediamine, phenylenediamine and the like can be used);

iridium complexes: [IrCl(L)]$_2$, [IrEr(L)]$_2$, [IrI(L)]$_2$, [IrCp*(L)]$_2$, [Ir(cod)(L)]OTf, [Ir(cod)(L)]BF$_4$, [Ir(cod)(L)]ClO$_4$, [Ir(cod)(L)]PF$_6$, [Ir(cod)(L)]SbF$_6$, [Ir(cod)(L)]BPh$_4$, [Ir(nbd)(L)]B$\{3,5$-$(CF_3)_2C_6H_3\}_4$, [Ir(nbd)(L)]OTf, [Ir(nbd)(L)]BF$_4$, [Ir(nbd)(L)]ClO$_4$, [Ir(nbd)(L)]PF$_6$, [Ir(nbd)(L)]SbF$_6$, [Ir(nbd)(L)]BPh$_4$, [Ir(nbd)(L)]B$\{3,5$-$(CF_3)_2C_6H_3\}_4$;

palladium complexes: [PdCl$_2$(L)], [PdBr$_2$(L)], [PdI$_2$(L)], [Pd(π-allyl)(L)]Cl, [Pd(π-allyl)(L)]OTf, [Pd(π-allyl)(L)]BF$_4$, [Pd(π-allyl)(L)]ClO$_4$, [Pd(π-allyl)(L)]PF$_6$, [Pd(π-allyl)(L)]BPh$_4$, [Pd(L)](OTf)$_2$, [Pd(L)](BF$_4$)$_2$, [Pd(L)](ClO$_4$)$_2$, [Pd(L)](PF$_6$)$_2$, [Pd(L)(BPh$_4$)$_2$, [Pd(L)$_2$], [Pd(L)$_2$](OAc)$_2$, [Pd(L)(H$_2$O)$_2$](OTf)$_2$, [Pd(L)(H$_2$O)$_2$](BF$_4$)$_2$, [Pd(L)(H$_2$O)$_2$](ClO$_4$)$_2$, Pd(L)(H$_2$O)$_2$](PF$_6$)$_2$, [Pd(L)(H$_2$O)$_2$](BPh$_4$)$_2$, [{Pd(L)}$_2$(μ-OH)$_2$](OTf)$_2$, [{Pd(L)}$_2$(μ-OH)$_2$](BF$_4$)$_2$, [{Pd(L)}$_2$(μ-OH)$_2$](ClO$_4$)$_2$, [{Pd(L)}$_2$(μ-OH)$_2$](PF$_6$)$_2$, [{Pd(L)}$_2$(μ-OH)$_2$](BPh$_4$)$_2$;

nickel complexes: [NiCl$_2$(L)], [NiBr$_2$(L)], [NiI$_2$(L)], [Ni(π-allyl)(L)]Cl, [Ni(cod)(L)], [Ni(nbd)(L)];

copper complexes: [CuCl(L)], [CuBr(L)], [CuI(L)], [CuH(L)], [Cu ($\eta^1$-BH$_4$)(L)], [Cu(Cp)(L)],[Cu(Cp*)(L)], [Cu(L)(CH$_3$CN)$_2$]OTf, [Cu(L)(CH$_3$CN)$_2$]BF$_4$, [Cu(L)(CH$_3$CN)$_2$]ClO$_4$, [Cu(L)(CH$_3$CN)$_2$]PF$_6$, [Cu(L)(CH$_3$CN)$_2$]BPh$_4$.

Examples of the above-mentioned diphosphine ligand represented by L include 2,2'-bis(diphenylphosphino)-1,1'-binaphthyl (hereinafter sometimes to be abbreviated as BINAP); BINAP derivatives having substituent(s) such as a $C_{1-6}$ alkyl group, a $C_{6-14}$ aryl group and the like on the naphthyl ring(s) of BINAP, for example, 2,2'-bis(diphenylphosphino)-6,6'-dimethyl-1,1'-binaphthyl;

BINP derivatives wherein the naphthyl ring(s) of BINAP is/are partially hydrogenated, for example, 2,2'-bis(diphenylphosphino)-5,6,7,8,5',6',7',8'-octahydro-1,1'-binaphthyl (H8-BINAP);

BINAP derivatives having 1 to 5 substituents such as a $C_{1-6}$ alkyl group, a halogen atom, a mono- or di-$C_{1-6}$ alkylamino group, a $C_{1-6}$ alkoxy group, a pyrrolidinyl group and the like on the benzene ring(s) bonded to the phosphorus atom of BINAP, for example, 2,2'-bis[bis(4-chlorophenyl)phosphino)-1,1'-binaphthyl, 2,2'-bis(di-p-tolylphosphino)-1,1'-binaphthyl (tol-BINAP), 2,2'-bis[bis(3,5-dimethylphenyl)phosphino]-1,1'-binaphthyl (xyl-BINAP), 2,2'-bis[bis(3,5-diethylphenyl)phosphino]-1,1'-binaphthyl, 2,2'-bis[bis(3,5-diisopropylphenyl) phosphino]-1,1'-binaphthyl, 2,2'-bis[bis(3,5-di-tert-butylphenyl)phosphino]-1,1'-binaphthyl, 2,2'-bis[bis(4-dimethylaminophenyl)phosphino]-1,1'-binaphthyl, 2,2'-bis[bis(4-dimethylamino-3,5-dimethylphenyl) phosphino]-1,1'-binaphthyl, 2,2'-bis[bis(4-dimethylamino-3,5-diethylphenyl)phosphino]-1,1'-binaphthyl, 2,2'-bis[bis(4-dimethylamino-3,5-diisopropylphenyl)phosphino]-1,1'-binaphthyl, 2,2'-bis [bis(4-diethylaminophenyl)phosphino]-1,1'-binaphthyl, 2,2'-bis[bis[4-(pyrrolidin-1-yl)phenyl]phosphino]-1,1'-binaphthyl, 2,2'-bis(di-p-methoxyphenylphosphino)-1,1'-binaphthyl, 2,2'-bis[bis(3,5-dimethyl-4-methoxyphenyl) phosphino]-1,1'-binaphthyl, 2,2'-bis[bis(3,5-di-tert-butyl-4-methoxyphenyl)phosphino]-1,1'-binaphthyl (DTBM-BINAP);

2,2'-bis(dicyclohexylphosphino)-6,6'-dimethyl-1,1'-biphenyl (BICHEP),2,2'-bis(diphenylphosphino)-6,6'-dimethoxybiphenyl (MeO-BIPHEP),2,3-bis(diphenylphosphino)butane (CHIRAPHOS), 1-cyclohexyl-1,2-bis(diphenylphosphino)ethane (CYCPHOS), 1,2-bis[(2-methoxyphenyl)phenylphosphino]ethane (DIPAMP), 1,2-bis(diphenylphosphino)propane (PROPHOS), 2,4-bis(diphenylphosphino)pentane (SKEWPHOS), SKEWPHOS derivative having 1 to 5 substituents such as a $C_{1-6}$ alkyl group and the like on the benzene ring(s) bonded to the phosphorus atom of SKEWPHOS, 1-[1',2-bis(diphenylphosphino)ferrocenyl]ethylenediamine (BPPFA), 1-substituted-3,4-bis(diphenylphosphino)pyrrolidine (DEGPHOS), 2,3-O-isopropylidene-2,3-dihydroxy-1,4-bis(diphenylphosphino)butane (DIOP), substituted-1, 2-bisphosphoranobenzene (DuPHOS), substituted-1,2-bisphosphoranoethane (BPE), 5,6-bis(diphenylphosphino)-2-norbornene (NORPHOS), N,N'-bis(diphenylphosphino)-N,N'-bis(1-phenylethyl) ethylenediamine (PNNP), 2,2'-diphenylphosphino-1,1'-bicyclopentyl (BICP), 4,12-bis(diphenylphosphino)-[2,2]-paracyclophane (PhanePHOS), N-substituted-N-diphenylphosphino-1-[2-(diphenylphosphino)ferrocenyl] ethylamine (BoPhoz), 1-[2-(disubstitutedphosphino)ferrocenyl]ethyl-disubstitutedphosphine (Josiphos), 1-[2-(2'-disubstitutedphosphinophenyl)ferrocenyl]ethyl-disubstitutedphosphine (Walphos), 2,2'-bis($\alpha$-N,N-dimethylaminophenylmethyl)-1,1'-bis(disubstitutedphosphino)ferrocene (Mandyphos), disubstitutedphosphino-2-[$\alpha$-(N,N-dimethylamino)-o-disubstitutedphosphinophenyl-methyl] ferrocene (Taniaphos), 1,1-bis(disubstituted-phosphotano)ferrocene (FerroTANE), 7,7'-bis(diphenylphosphino)-3,3',4,4'-tetrahydro-4,4'-dimethyl-8,8'-bi(2H-1,4-benzoxazine) (Solphos) and the like.

The above-mentioned diphosphine ligand represented by L is preferably an optically active form.

An optically active ligand is used as the "ligand" for the "transition metal complex".

The "transition metal complex" can be produced from a ligand and the other complex as a transition metal source according to a known method (productions of rhodium complexes; Journal of the American Chemical Society (J. Am. Chem. Soc.), vol. 94, page 6429, 1972, Organic Synthesis (Org. Synth.), vol. 67, page 33, 1989: productions of ruthenium complexes; Journal of Organic Chemistry (J. Org. Chem.), vol. 57, page 4053, 1992, Tetrahedron Asymmetry (Tetrahedron Asym.), vol. 2, page 43, 1991, Journal of Organic Chemistry (J. Org. Chem.), vol. 59, page 3064, 1994, Angewandte Chemie International Edition (Angew. Chem., Int. Ed.), vol. 37, page 1703, 1998: productions of iridium complexes; Journal of Organometallic Chemistry (J. Organomet. Chem.), vol. 428, page 213, 1992: productions of palladium complexes; Organometallics (Organometallics), vol. 12, page 4188, 1993, Journal of the American Chemical Society (J. Am. Chem. Soc.), vol. 121, page 5450, 1999: productions of nickel complexes; "5th Ed., Jikken Kagaku Koza" edited by Japan Chemical Society (Maruzen), vol. 21, organic transition metal compound, supermolecular complex, pages 293-294 (2004): productions of copper complexes; "5th Ed., Jikken Kagaku Koza" edited by Japan Chemical Society (Maruzen), vol. 21, organic transition metal compound, supermolecular complex, page 357 (2004), Journal of Organic Chemistry (J. Org. Chem.), vol. 63, page 6090, 1998), and can be isolated or purified by a known means (e.g., concentration, solvent extraction, fractional distillation, crystallization, recrystallization, chromatography).

Among the "diphosphine ligand" represented by L, SKEWPHOS derivative having 1 to 5 substituents such as a $C_{1-6}$ alkyl group and the like on the one benzene ring bonded to the phosphorus atom of SKEWPHOS can be synthesized according to the method described in the Patent Document WO 2013/146987.

The "transition metal complex" can also be prepared by adding a "ligand" and the other complex as a transition metal source to a reaction system. The "transition metal complex" may be directly added to a reaction container, or may be prepared by adding the above-mentioned "transition metal" and "ligand" to a container. When the "transition metal complex" is prepared by adding the "transition metal" and "ligand" to a container, the "ligand" is used in an amount of 1- to 100-fold by mole, preferably 1 to 5-fold by mole, further more preferably 1.01 to 2.02-fold by mole, relative to the theoretical mole required to prepare the "transition metal complex".

For example, the rhodium complex of SKEWPHOS derivative having 1 to 5 substituents such as a $C_{1-6}$ alkyl group and the like on the one benzene ring bonded to the phosphorus atom of SKEWPHOS, among the "diphosphine ligand" represented by L, can be synthesized according to the method described in the Patent Document WO 2013/146987.

In addition, the "transition metal complex" is preferably a ruthenium complex represented by the formula:

$$[Ru(OCOR^a)_2L^a] \quad (VIII)$$

wherein
$R^a$ is an optionally substituted $C_{1-3}$ alkyl group; and
$L^a$ is a diphosphine ligand,
which is exemplified by $[Ru(OAc)_2(L)]$ or $[Ru(OCOCF_3)_2(L)]$, among the "ruthenium complexes".

Preferable examples of the "$C_{1-3}$ alkyl group" of the "optionally substituted $C_{1-3}$ alkyl group" represented by $R^a$ include methyl, ethyl and isopropyl, and methyl is particularly preferable.

The "$C_{1-3}$ alkyl group" of the "optionally substituted $C_{1-3}$ alkyl group" represented by $R^a$ each optionally has 1 to 5 (preferably 1 to 3) substituents at substitutable position(s). Examples of the substituent include the above-mentioned the above-mentioned Substituent Group A. The substituent is preferably a halogen atom, more preferably a fluorine atom. When the number of the substituents is plural, the respective substituents may be the same or different.

The "optionally substituted $C_{1-3}$ alkyl group" represented by $R^a$ is preferably methyl or trifluoromethyl, more preferably trifluoromethyl.

Examples of the diphosphine ligand represented by $L^a$ include those similar to the diphosphine ligands exemplified as L; among them, preferred are 2,2'-bis(diphenylphosphino)-1,1'-binaphthyl (hereinafter sometimes to be abbreviated as BINAP);
BINAP derivatives having substituent(s) such as a $C_{1-6}$ alkyl group, a $C_{6-14}$ aryl group and the like on the naphthyl ring(s) of BINAP, for example, 2,2'-bis(diphenylphosphino)-6,6'-dimethyl-1,1'-binaphthyl; BINAP derivatives wherein the naphthyl ring(s) of BINAP is/are partially hydrogenated, for example, 2,2'-bis (diphenylphosphino)-5,6,7,8,5',6',7',8'-octahydro-1,1'-binaphthyl (H8-BINAP); BINAP derivatives having 1 to 5 substituents such as a $C_{1-6}$ alkyl group and the like on the one benzene ring bonded to the phosphorus atom of BINAP, for example, 2,2'-bis(di-p-tolylphosphino)-1,1'-binaphthyl (tol-BINAP), 2,2'-bis[bis(3,5-dimethylphenyl)phosphino]-1,1'-binaphthyl (xyl-BINAP), 2,2'-bis[bis(3,5-diethylphenyl)phosphino]-1,1'-binaphthyl, 2,2'-bis[bis(3,5-diisopropylphenyl)phosphino]-1,1'-binaphthyl, 2,2'-bis[bis(3,5-di-tert-butylphenyl)phosphino]-1,1'-binaphthyl, 2,2'-bis[bis(4-dimethylaminophenyl)phosphino]-1,1'-binaphthyl, 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl, 2,2'-bis[bis(4-dimethylamino-3,5-diisopropylphenyl)phosphino]-1,1'-binaphthyl, 2,2'-bis[bis(4-diethylaminophenyl)phosphino]-1,1'-binaphthyl and 2,2'-bis[bis[4-(pyrrolidin-1-yl)phenyl]phosphino]-1,1'-binaphthyl, 2,2'-bis(di-p-methoxyphenylphosphino)-1,1'-binaphthyl, 2,2'-bis[bis(3,5-dimethyl-4-methoxyphenyl)phosphino]-1,1'-binaphthyl, 2,2'-bis[bis(3,5-di-tert-butyl-4-methoxyphenyl)phosphino]-1,1'-binaphthyl (DTBM- BINAP), 4,12-bis(diphenylphosphino)-[2,2]-paracyclophane (PhanePHOS), and 2,2'-bis(α-N,N-dimethylaminophenylmethyl)-1,1'-bis(disubstitutedphosphino)ferrocene (Mandyphos);

more preferred are 2,2'-bis(diphenylphosphino)-1,1'-binaphthyl, 2,2'-bis[bis(4-chlorophenyl)phosphino]-1,1'-binaphthyl, and 2,2'-bis(α-N,N-dimethylaminophenylmethyl)-1,1'-bis(disubstitutedphosphino)ferrocene (Mandyphos); and further more preferred are 2,2'-bis[bis(4-chlorophenyl)phosphino]-1,1'-binaphthyl, and 2,2'-bis(α-N,N-dimethylaminophenylmethyl)-1,1'-bis(disubstitutedphosphino)ferrocene (Mandyphos).

The ruthenium complex represented by the formula (VIII) is preferably a ruthenium complex represented by the formula:

[Ru(OCOR$^{a1}$)$_2$L$^{a1}$]   (VIII')

wherein

R$^{a1}$ is a trifluoromethyl group; and

L$^{a1}$ is an optically active diphosphine ligand selected from (1) an optically active form consisting of a compound represented by the formula:

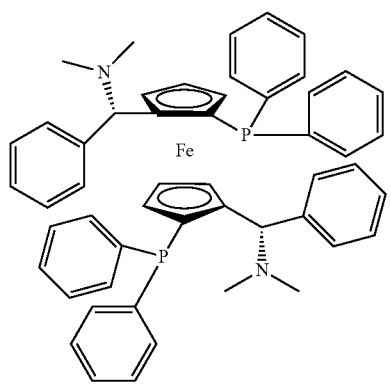

(IX-a)

(Rp,S)-Mandyphos or the formula:

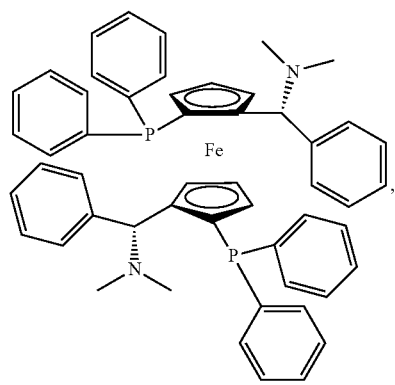

(IX-b)

(Sp,R)-Mandyphos or a mixture thereof, and (2) an optically active form of a compound represented by the formula:

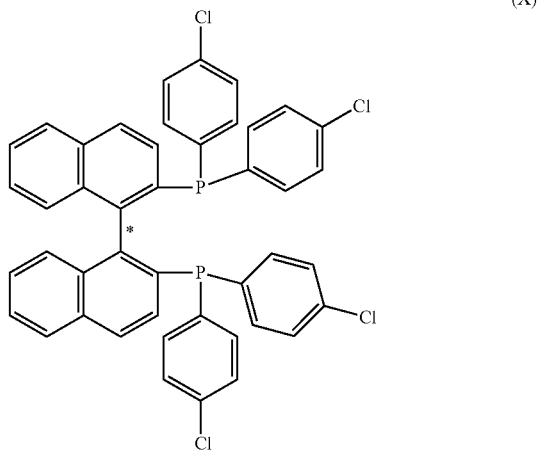

(X)

wherein the bond marked with * is a chiral axis.

The optically active form consisting of the above-mentioned mixture means that a mixture (excluding a mixture of 1 mol: 1 mol) of ruthenium complex (VIII') wherein L$^{a1}$ is an optically active compound represented by the formula (IX-a) and ruthenium complex (VIII') wherein L$^{a1}$ is an optically active compound represented by the formula (IX-b) is used as a ruthenium complex.

The ruthenium complex represented by the formula (VIII) or (VIII') can be synthesized, for example, by reference to the method described in JP-A-S62-265293, Tetrahedron Lettes, 39, page 4441, 1998 or the like.

These ruthenium complexes are useful as a catalyst with high reaction selectivity in various hydrogenation reactions such as Production Method (A) and the like.

Preferable specific examples of the ruthenium complex include the followings: [Ru(OCOCF$_3$)$_2${(S)-p-Cl-binap}], [Ru(OCOCF$_3$)$_2${(S)-(R)-mandyphos}], [RuCl$_2$(S)-binap], [Ru(OCOCF$_3$)$_2${(S)-binap}] and [Ru(OCOCF$_3$)$_2${(S)-phanephos}]. Among the, [Ru(OCOCF$_3$)$_2${(S)-binap}] and [Ru(OCOCF$_3$)$_2${(S)-(R)-mandyphos}] are preferable.

While the amount of the "transition metal complex" to be used varies depending on the reaction container, reaction procedure and the like, it is, for example, about 1.0-about 0.00001 mol per 1 mol of the compound represented by the formula (I) or a salt thereof, which is a substrate.

In the "hydrogenation reaction" in Production Method (A), hydrogen gas, metal hydride, isopropanol, formic acid, benzthiazoline, Hantzsch ester and the like can be used as a hydrogen donor. Among them, hydrogen gas is preferably used.

When hydrogen gas is used, the hydrogenation reaction can be carried out by batch process or continuous process. When the hydrogenation reaction is carried out in the presence of hydrogen gas, the hydrogen pressure is, for example, 0.001 to 200 atm, preferably 0.1 to 15 atm.

In the "hydrogenation reaction" in Production Method (A), an additive such as a base, an acid, a salt and the like may be added, if necessary. The additive may be used in a mixture of two or more kinds thereof. The additive may be added to a reaction container before or during the "hydrogenation reaction".

Examples of the base that may be added for the "hydrogenation reaction" in Production Method (A) include inorganic bases and organic bases.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogencarbonate, potassium hydrogencarbonate and the like; acetates such as sodium acetate, potassium acetate and the like; phosphorates such as tripotassium phosphate, sodium phosphate and the like; and hydrogenphosphates such as dipotassium hydrogenphosphate, disodium hydrogenphosphate and the like.

Examples of the organic base include aliphatic amines such as trimethylamine, triethylamine, N-methylmorpholine, N,N-diisopropylethylamine, diethylamine, diisopropylamine, cyclohexylamine, ethylenediamine and the like; aromatic amines such as pyridine, picoline, N,N-dimethylaniline and the like; and basic amino acids such arginine, lysine, ornithine and the like.

While the amount of the base to be used varies depending on the kind of the solvent and the other reaction conditions, it is generally about 0.01 mol or more per 1 mol of the compound represented by the formula (I) or a salt thereof, which is a substrate. The base may be used as a solvent.

Examples of the acid that may be added for the "hydrogenation reaction" in Production Method (A) include mineral acids (specifically hydrofluoric acid, hydrochloric acid, hydrobromic acid, hydriodic acid, nitric acid, sulfuric acid, sulfurous acid, phosphoric acid, phosphorous acid, carbonic acid, bicarbonic acid and the like); carboxylic acids (i.e., compounds having one or more carboxy groups; specifically formic acid, acetic acid, trifluoroacetic acid, benzoic acid, phthalic acid, fumaric acid, oxalic acid, tartaric acid, maleic acid, citric acid, succinic acid, malic acid and the like); acidic amino acids (specifically aspartic acid, glutamic acid and the like); and sulfonic acids (i.e., compounds having one or more sulfo groups; specifically methanesulfonic acid, trifluoromethanesulfonic acid, benzenesulfonic acid, p-toluenesulfonic acid, camphorsulfonic acid and the like). These may be used in a mixture of two or more kinds thereof, in necessary. Preferable examples of the acid that may be added for the "hydrogenation reaction" in Production Method (A) include sulfonic acid and sulfuric acid; and sulfonic acid is more preferable.

The sulfonic acid means a compound having one or more sulfo groups, and is preferably the above-mentioned sulfonic acid represented by the formula (VII); more preferably methanesulfonic acid, trifluoromethanesulfonic acid, benzenesulfonic acid or p-toluenesulfonic acid; particularly preferably p-toluenesulfonic acid.

While the amount of the acid to be used varies depending on the kind of the solvent and the other reaction conditions, it is generally about 0.01 mol or more per 1 mol of the compound represented by the formula (I) or a salt thereof, which is a substrate. The acid may be used as a solvent. The amount thereof is preferably 0.05 to 1.5 mol.

Examples of the salt that may be added for the "hydrogenation reaction" in Production Method (A) include, in addition to the salts exemplified in the above-mentioned "inorganic base", salts containing the above-mentioned "acid" used for the "hydrogenation reaction" as an acid component. Among them, salts containing a halogen anion are preferable, and examples thereof include alkali metal halides and a compound represented by the formula:

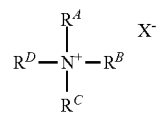

(VI)

wherein
$R^A$, $R^B$, $R^C$ and $R^D$ are independently a hydrogen atom, or an optionally substituted hydrocarbon group; and
X is a halogen atom,
and the like.

Preferable examples of the "hydrocarbon group" of the "optionally substituted hydrocarbon group" represented by $R^A$, $R^B$, $R^C$ or $R^D$ include a $C_{1-6}$ alkyl group, a $C_{3-10}$ cycloalkyl group, a $C_{6-14}$ aryl group, a $C_{7-16}$ aralkyl group and the like. The "hydrocarbon group" of the "optionally substituted hydrocarbon group" represented by $R^A$, $R^B$, $R^C$ or $R^D$ is particularly preferably n-butyl.

The "alkali metal halide" exemplified as the "salt" that may be added for the "hydrogenation reaction" in Production Method (A) means a salt consisting of a halogen atom (e.g., chlorine, bromine, iodine) which is an anion, and an alkali metal (e.g., lithium, sodium, potassium, cesium) which is a cation, and among them, preferred are lithium bromide, sodium bromide, potassium bromide, lithium chloride, sodium chloride, potassium chloride, lithium iodide, sodium iodide and potassium iodide; more preferred are lithium bromide, sodium bromide, potassium bromide, lithium chloride, sodium chloride and potassium chloride; and particularly preferred is potassium bromide. The "alkali metal halide" may be a hydrate.

Preferable examples of the above-mentioned compound represented by the formula (VI) include tetrabutylammonium bromide, tetrabutylammonium chloride, tetrabutylammonium iodide and n-butylammonium chloride.

While the amount of the compound (a salt having a halogen anion) to be used varies depending on the kind of the solvent and the other reaction conditions, it is generally 1 to 100 equivalent, preferably 2 to 20 equivalent, relative to the organic metal complex.

The "salt" that may be added for the "hydrogenation reaction" in Production Method (A) is preferably an alkali metal halide; and potassium bromide is particularly preferable.

The "hydrogenation reaction" in Production Method (A) is generally carried out in a solvent. The solvent is not particularly limited as long as it does not inhibit the reaction and dissolves the raw material compound, organic metal complex and additive. Examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, isopropanol, n-butanol, 2-butanol, tert-butanol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethylmethylketone, methylisopropylketone, methylbutylketone and the like; esters such as ethyl acetate, isopropyl acetate, n-propyl acetate, n-butyl acetate, isobutyl acetate, methyl acetate, ethyl formate and the like; nitromethane; water and the like. These solvents may be used as a mixture in an appropriate ratio. Preferable examples of the solvent to be used for the "hydrogenation reaction" in Production Method (A) include alcohols. Among the, methanol, ethanol and isopropanol are preferable, and isopropanol is particularly preferable.

The amount of the solvent to be used is appropriately determined depending on the solubility of the compound represented by the formula (I) or a salt thereof, which is a substrate, and the like. For example, when an alcohol (preferably isopropanol) is used as a solvent, the reaction can be carried out from nearly in absence of a solvent to in a 100-fold by weight or more of solvent, relative to the compound represented by the formula (I) or a salt thereof, which is a substrate. Generally, the solvent is preferably used in an amount of about 2- about 100-fold by weight, relative to the compound represented by the formula (I) or a salt thereof, which is a substrate.

In the "hydrogenation reaction" in Production Method (A), the reaction temperature is generally −30 to 160° C., preferably 0 to 120° C., more preferably 10 to 80° C. The reaction time is generally 0.1 to 120 hr, preferably 1 to 72 hr.

The optically active form of the compound represented by the formula (II) or a salt thereof obtained by the "hydrogenation reaction" may be purified by a known means (e.g., fractional recrystallization method, chiral column method, diastereomer salt method). In order to obtain the optically active form of the compound represented by the formula (II) or a salt thereof with high optical purity, it is preferably purified by fractional recrystallization method or diastereomer salt method. When the optically active form of the compound represented by the formula (II) or a salt thereof is optically active piperidine-3-carboxamide p-toluenesulfonate, it is particularly preferably directly purified by fractional recrystallization method.

The compound represented by the formula (I) can be synthesized, for example, according the method described in Journal of Organic Chemistry (J. Org. Chem.), vol. 31, page 2487, 1966 or Journal of Organic Chemistry (J. Org. Chem.), vol. 33, page 747, 1968.

Production Method (A) can be employed for producing an optically active form of a compound having more complicated structure or a salt thereof in combination with other reaction.

The production method of the optically active form of the compound represented by the formula (V) or a salt thereof employing Production Method (A) is explained below.

[Production Method (B)]

The optically active form of the compound represented by the formula (V) or a salt thereof can be produced according to Production Method (B) shown in the following reaction scheme.

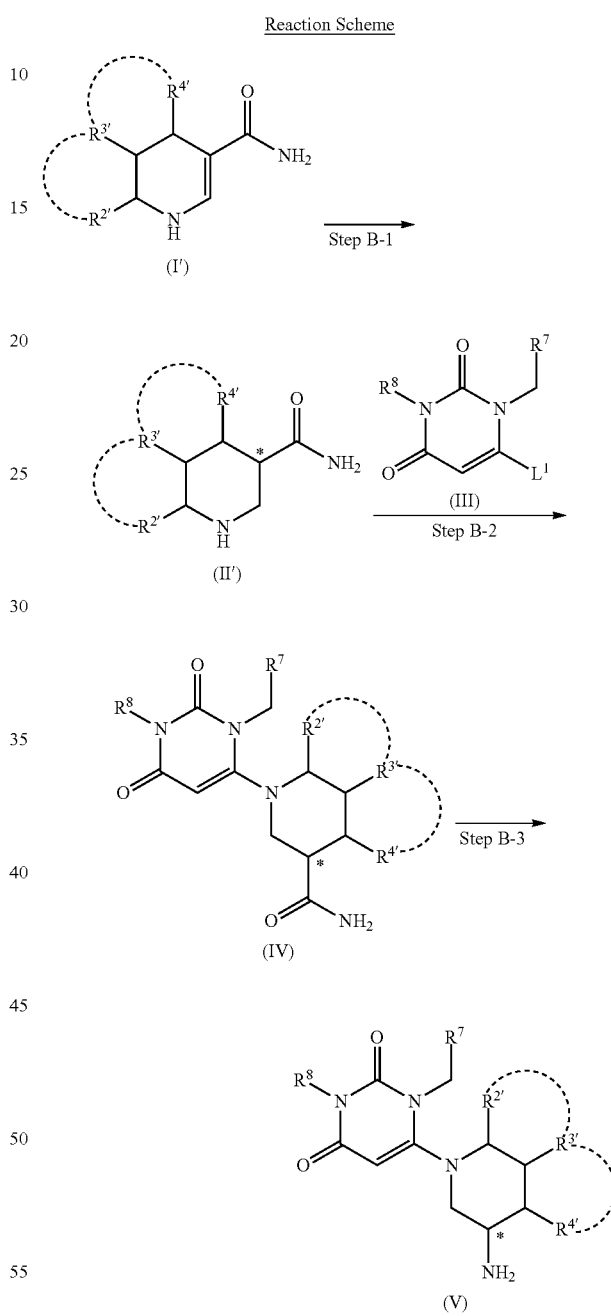

wherein each symbol is as defined above.

The reagents and conditions used for Production Method (B) are explained in detail each step below.

[Step B-1]

Step B-1 is a step of producing the optically active form of the compound represented by the formula (II') or a salt thereof by subjecting the compound represented by the formula (I') or a salt thereof to an asymmetric hydrogenation reaction, as shown in the following reaction scheme.

Reaction Scheme

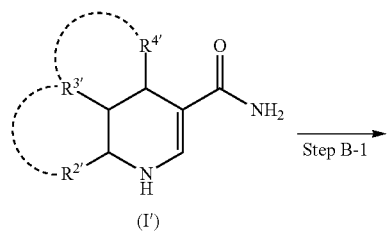

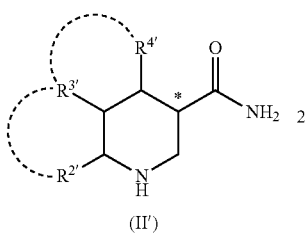

wherein each symbol is as defined above.

The asymmetric hydrogenation reaction of Step B-1 is carried out in the same manner as in Production Method (A), except that the compound represented by the formula (I') is used instead of the compound represented by the formula (I), and thereby, the optically active form of the compound represented by the formula (II') is produced instead of the optically active form of the compound represented by the formula (II).

The compound represented by the formula (I') can be synthesized, for example, according to the method described in Journal of Organic Chemistry (J. Org. Chem.), vol. 31, page 2487, 1966 or Journal of Organic Chemistry (J. Org. Chem.), vol. 33, page 747, 1968.

[Step B-2]

Step B-2 is a step of producing the optically active form of the compound represented by the formula (IV) or a salt thereof by subjecting the optically active form of the compound represented by the formula (II') or a salt thereof obtained in Step 5-1 to a condensation reaction with the compound represented by the formula (III) or a salt thereof, as shown in the following reaction scheme.

Reaction Scheme

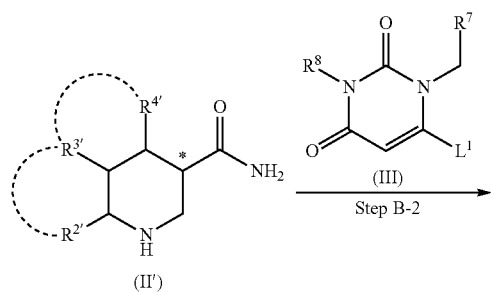

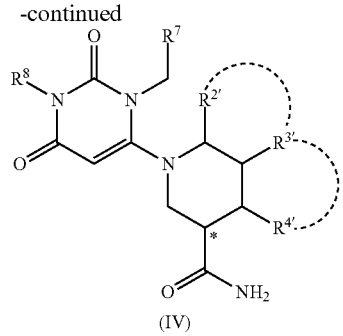

wherein each symbol is as defined above.

The compound represented by the formula (III) can be synthesized, for example, according to the method described in WO 2007/035629.

While the amount of the compound represented by the formula (III) or a salt thereof to be used varies depending on the kind of the solvent and the other reaction conditions, it is generally 0.01 to 100 mol, preferably 0.1 to 10 mol, more preferably 0.9 to 1.1 mol, per 1 mol of the optically active form of the compound represented by the formula (II') or a salt thereof 1 mol.

The reaction of Step E-2 is generally carried out in a solvent, and a base may be added for the progress of the reaction. The solvent is not particularly limited as long as it does not inhibit the reaction and dissolves the raw material compound, organic metal complex and additive. Examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, isopropanol, n-butanol, 2-butanol, tert-butanol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, chloroform, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethylmethylketone, methylisopropylketone, methylbutylketone and the like; esters such as ethyl acetate, isopropyl acetate, n-propyl acetate, n-butyl acetate, isobutyl acetate, methyl acetate, ethyl formate and the like; nitromethane; water and the like. These solvents may be used as a mixture in an appropriate ratio. Preferable examples of the solvent to be used in Step B-2 include alcohols. Among them, isopropanol is particularly preferable. When isopropanol is used as a solvent, it is preferably used in a mixed solvent with water, and the volume ratio is preferably isopropanol:water=9:0.01 to 1:9.

The amount of the solvent to be used is appropriately determined depending on solubility of the optically active form of the compound represented by the formula (II') or a salt thereof, and the like. For example, when an alcohol (preferably isopropanol) is used as a solvent, the reaction can be carried out from nearly in absence of a solvent to in a 100-fold by weight or more of solvent, relative to the optically active form of the compound represented by the formula (II') or a salt thereof, which is a substrate. Generally, the solvent is preferably used in an amount of about 2-about 100-fold by weight, relative to the optically active form of the compound represented by the formula (II') or a salt thereof, which is a substrate.

Examples of the base that may be used in Step B-2 include inorganic bases and organic bases.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogencarbonate, potassium hydrogencarbonate and the like; acetates such as sodium acetate, potassium acetate and the like; phosphorates such as tripotassium phosphate, sodium phosphate and the like; and hydrogenphosphates such as dipotassium hydrogenphosphate, disodium hydrogenphosphate and the like.

Examples of the organic base include aliphatic amines such as trimethylamine, triethylamine, N-methylmorpholine, N,N-diisopropylethylamine, diethylamine, diisopropylamine, cyclohexylamine, ethylenediamine, 1,8-diazabicyclo[5.4.0]undecene and the like; aromatic amines pyridine, picoline, N,N-dimethylaniline and the like; and basic amino acids such as arginine, lysine, ornithine and the like.

The base that may be used in Step B-2 is particularly preferably potassium carbonate.

While the amount of the base to be used varies depending on the kind of the solvent and the other reaction conditions, it is generally about 0.01 mol or more, per 1 mol of the optically active form of the compound represented by the formula (II') or a salt thereof. The base may be used as a solvent. The amount of the base to be used is preferably 0.5 to 10 mol, more preferably 1 to 5 mol, per 1 mol of the optically active form of the compound represented by the formula (II') or a salt thereof.

The reaction temperature is generally −30° C. to 160° C., preferably 0 to 120° C., more preferably 30 to 90° C. The reaction time is generally 0.1 to 120 hr, preferably 1 to 72 hr.

The optically active form of the compound represented by the formula (IV) or a salt thereof obtained in Step B-2 may be purified by a known means (e.g., fractional recrystallization method, chiral column method, diastereomer salt method).

[Step B-3]

Step B-3 is a step of producing the optically active form of the compound represented by the formula (V) or a salt thereof by subjecting the optically active form of the compound represented by the formula (IV) or a salt thereof to a rearrangement reaction, as shown in the following reaction scheme.

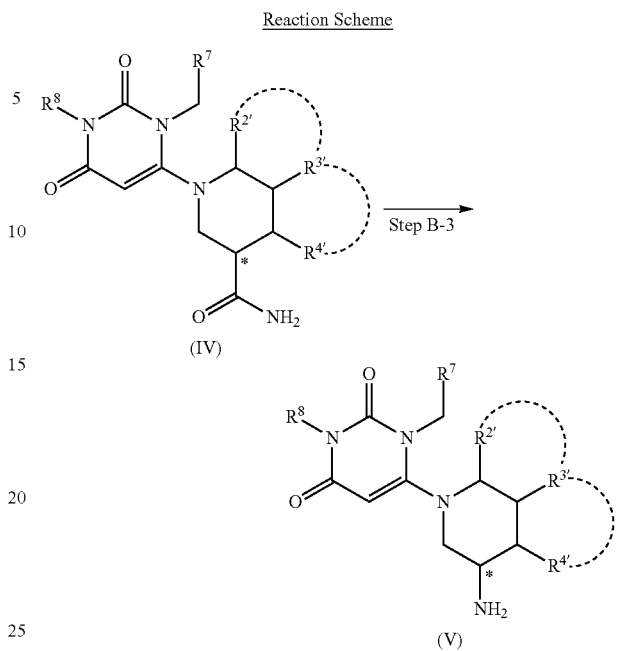

Reaction Scheme wherein each symbol is as defined above.

The rearrangement reaction of Step B-3 is preferably carried out using an oxidant. Examples of the "oxidant" include hypohalites such as potassium hypochlorite, sodium hypochlorite, tert-butyl hypochlorite, potassium hypobromite, sodium hypobromite, potassium hypoiodite, sodium hypoiodite and the like; lead tetraacetate; halogens such as bromine, iodine and the like; halogenated imide reagents such as N-bromosuccinimide, N-iodosuccinimide and the like; hypervalent iodine reagents such as iodobenzene diacetate, [bis(trifluoroacetoxy)iodo]benzene, iodotoluenediacetate, [bis(trifluoroacetoxy)iodo]toluene and the like, and the like. Preferable examples of the oxidant to be used for the rearrangement reaction of Step B-3 include hypervalent iodine reagents. Among them, iodobenzene diacetate is more preferable.

While the amount of the oxidant to be used varies depending on the kind of the solvent and the other reaction conditions, it is generally 0.01 to 100 mol, preferably 0.1 to 10 mol, more preferably 0.9 to 2 mol, per 1 mol of the optically active form of the compound represented by the formula (IV) or a salt thereof.

In the rearrangement reaction of Step B-3, an additive such as a base, an acid, a salt and the like may be added. The additive may be used in a mixture of two or more kinds thereof, if necessary. The additive may be added to a reaction container before or during the rearrangement reaction.

Examples of the base that may be added for the rearrangement reaction of Step B-3 include inorganic bases and organic bases.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogencarbonate, potassium hydrogencarbonate and the like; acetates such as sodium acetate, potassium acetate and the like; phosphorates such as tripotassium phosphate, sodium phosphate and the like; and hydrogenphosphates such as dipotassium hydrogenphosphate, disodium hydrogenphosphate and the like.

Examples of the organic base include aliphatic amines such as trimethylamine, triethylamine, N-methylmorpholine, N,N-diisopropylethylamine, diethylamine, diisopropylamine, cyclohexylamine, ethylenediamine, 1,8-diazabicyclo[5.4.0]undecene and the like; aromatic amines such as pyridine, picoline, N,N-dimethylaniline and the like; and basic amino acids such as arginine, lysine, ornithine and the like.

While the amount of the base to be used varies depending on the kind of the solvent and the other reaction conditions, it is generally about 0.001 mol or more, preferably 0.001 to 10 mol, more preferably 0.01 to 2 mol, per 1 mol of the optically active form of the compound represented by the formula (IV) or a salt thereof, which is a substrate. The base may be used as a solvent.

Examples of the acid that may be added for the rearrangement reaction of Step B-3 include mineral acids such as hydrofluoric acid, hydrochloric acid, hydrobromic acid, hydriodic acid, nitric acid, sulfuric acid, sulfurous acid and the like; phosphoric acid, phosphorous acid, carbonic acid, bicarbonic acid; carboxylic acids such as formic acid, acetic acid, trifluoroacetic acid, phthalic acid, fumaric acid, oxalic acid, tartaric acid, maleic acid, citric acid, succinic acid, malic acid and the like; acidic amino acids such as aspartic acid, glutamic acid and the like; and sulfonic acids such as methanesulfonic acid, trifluoromethanesulfonic acid, benzenesulfonic acid, p-toluenesulfonic acid, camphorsulfonic acid and the like. These may be used in a mixture of two or more kinds thereof, if necessary.

While the amount of the acid to be used varies depending on the kind of the solvent and the other reaction conditions, it is generally 0.001 mol or more, preferably 0.001 to 10 mol, more preferably 0.01 to 2 mol, per 1 mol of the optically active form of the compound represented by the formula (IV) or a salt thereof. The acid may be used as a solvent.

Examples of the salt that may be added for the rearrangement reaction of Step B-3 include, in addition to the salts exemplified in the above-mentioned "inorganic base", salts containing the above-mentioned "acid" used for the rearrangement reaction as an acid component. Among them, salts containing a halogen anion are preferable, and examples thereof include the above-mentioned alkali metal halides and the above-mentioned ammonium salt represented by the formula (VI), and the like.

While the amount of the salt to be used varies depending on the kind of the solvent and the other reaction conditions, it is generally about 0.001 mol or more, preferably 0.001 to 10 mol, more preferably 0.01 to 2 mol, per 1 mol of the optically active form of the compound represented by the formula (IV) or a salt thereof. The salt may be used as a solvent.

Preferable examples of the additive that may be added for the rearrangement reaction of Step B-3 include bases, and sodium hydroxide, pyridine, triethylamine, potassium carbonate, sodium hydrogencarbonate and ammonium chloride are more preferable, and pyridine is particularly preferable.

The reaction of Step B-3 is generally carried out in a solvent. The solvent is not particularly limited as long as it does not inhibit the reaction and dissolves the raw material compound, organic metal complex and additive. Examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, isopropanol, n-butanol, 2-butanol, tert-butanol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; halogenated hydrocarbons such as chloroform, dichloromethane, chloroform, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethylmethylketone, methylisopropylketone, methylbutylketone and the like; esters such as ethyl acetate, isopropyl acetate, n-propyl acetate, n-butyl acetate, isobutyl acetate, methyl acetate, ethyl formate and the like; nitromethane; water and the like. These solvents may be used as a mixture in an appropriate ratio. Preferable examples of the solvent to be used in Step B-3 include alcohols and nitriles. Among alcohols, ethanol and isopropanol are particularly preferable. When ethanol or isopropanol is used as a solvent, it is preferably used in a mixed solvent with water, and the volume ratio is preferably isopropanol:water=9:1 to 1:9. Among nitriles, acetonitrile is particularly preferable. When acetonitrile is used as a solvent, it is preferably used in a mixed solvent with water, and the volume ratio is preferably acetonitrile:water=9:1 to 1:9.

The amount of the solvent to be used is appropriately determined depending on the solubility of the optically active form of the compound represented by the formula (IV) or a salt thereof, and the like. For example, when an alcohol (preferably ethanol, isopropanol) or a nitrile (preferably acetonitrile) is used as a solvent, the reaction can be carried out from nearly in absence of a solvent to in a 100-fold by weight or more of Solvent, relative to the optically active form of the compound represented by the formula (IV) or a salt thereof. Generally, the solvent is preferably used in an amount of about 2-about 100-fold by weight, relative to the optically active form of the compound represented by the formula (IV) or a salt thereof, which is a substrate.

The reaction temperature is generally −30° C. to 160° C., preferably 0 to 80° C., more preferably 0 to 30° C. The reaction time is generally 0.1 to 120 hr, preferably 1 to 72 hr.

The optically active form of the compound represented by the formula (V) or a salt thereof obtained in Step 3-3 may be purified by a known means (e.g., fractional recrystallization method, chiral column method, diastereomer salt method).

EXAMPLES

The present invention is explained in detail in the following by referring to Reference Examples and Examples, which are merely exemplified and not to be construed as limitative, and the invention may be changed within the scope of the present invention.

In the following Reference Examples and Examples, the "room temperature" generally means about 10° C. to about 35° C. The chemical yield is an isolated yield (mol/mol %) or a yield measured by high-performance liquid chromatography. The optical purity (asymmetric yield) of an optically active form is evaluated by enantiomeric excess (% e.e.). The enantiomeric excess is calculated according to the following formula.

Enantiomeric excess (% e.e.)=100×[(R)−(S)]/[(R)+(S)] or 100×[(S)−(R)]/[(R)+(S)] wherein (R) and (S) are each an area of each enantiomer measured by high-performance liquid chromatography.

In addition, the amount of solvent used for chromatography is shown by % by volume, and the amount of the other is shown by % by weight.

In proton NMR spectrum, broad and unidentified protons such as OH and NH protons and the like are not described in data.

The abbreviations used in the specification mean the following.

s: singlet d: doublet t: triplet q: quartet m: multiplet br: broad

J: coupling constant

Hz: hertz $CDCl_3$: deuterochloroform

DMSO-$d_6$: deuterodimethyl sulfoxide $CD_3OD$: deuterated methanol $^1$H-NMR: proton nuclear magnetic resonance $^{13}$C-NMR: $^{13}$C nuclear magnetic resonance $^{19}$F-NMR: $^{19}$F nuclear magnetic resonance $^{31}$P-NMR: $^{31}$P nuclear magnetic resonance $RuCl_2${(S)-binap}: dichloro[(S)-(−)-2,2'-bis(diphenylphosphino)-1,1'-binaphthyl]ruthenium(II)

In the following Reference Examples and Examples, the nuclear magnetic resonance spectrum (NMR) was measured under the following conditions.

$^1$H nuclear magnetic resonance spectrum ($^1$H-NMR): BRUKER AVANCE 500 (500 MHz) manufactured by Bruker Corporation, internal standard material: tetramethylsilane $^{13}$C nuclear magnetic resonance spectrum ($^{13}$C-NMR): BRUKER AVANCE 500 (125 MHz) manufactured by Bruker Corporation, internal standard material: $CDCl_3$ $^{19}$F nuclear magnetic resonance spectrum ($^{19}$F-NMR): BRUKER AVANCE 500 (202 MHz) manufactured by Bruker Corporation, external standard material: trifluoroacetic acid $^{31}$P nuclear magnetic resonance spectrum ($^{31}$P-NMR): BRUKER AVANCE 500 (471 MHz) manufactured by Bruker Corporation, external standard material: 85%-$H_3PO_4$ aqueous solution Reference Example 1

Synthesis of 1,4,5,6-tetrahydropyridine-3-carboxamide

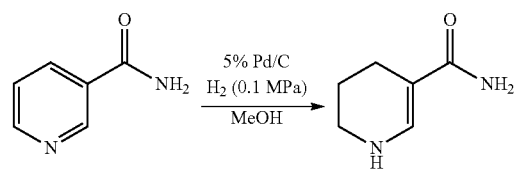 [SMILES: "MeOH" ; NC(=O)c1cccnc1 ; NC(=O)C1=CNCCC1]

Nicotinamide (50.00 g) [mw. 122.12, 0.409 mol], 5% Pd/C (5.00 g) and methanol (500 mL) were placed in an autoclave (1 L). The system was purged with hydrogen gas, and the mixture was stirred at 45° C. for 14 hr under constant hydrogen pressure (0.1 MPa). After the system was freed from pressure, the Pd/C was removed by filtration on hot through membrane filter, and the filtrate was concentrated under reduced pressure. To the residue was added methanol (100 mL), and the mixture was aged at room temperature for 1 hr, and filtered under reduced pressure. The substance collected by filtration was washed with methanol (50 mL), and dried at 50° C. under reduced pressure to give the desired compound. White crystalline powder, 35.52 g, yield 68%.

$^1$H-NMR (500 MHz, $CDCl_3$, TMS) δ (ppm) 1.72-1.76 (m, 2H), 2.15 (t, J=6.31 Hz, 2H), 3.05-3.15 (m, 2H), 7.38 (s, 1H).

(The protons derived from NH, OH and COOH were not detected)

$^{13}$C-NMR (125 MHz, $CDCl_3$, $CDCl_3$) δ(ppm) 20.03, 39.75, 94.15, 143.62, 173.99.

Anal. Calcd for $C_6H_{10}N_2O$: C, 57.12; H, 7.99; N, 22.21. Found: C, 57.11; H, 8.09; N, 22.10.

ESI-MS: m/z 127.0873 [M+H]$^+$.

IR(ATR, cm$^{-1}$):3300 (vNH), 3201 (vNH), 3000-2800 (vCH), 1622 (vC=O), 1506 (vC=C), 1423 (δCH), 1362 (δCH).

Example 1

Synthesis of 1,4,5,6-tetrahydropyridine-3-carboxamide p-toluenesulfonate 0.85 ethanolate

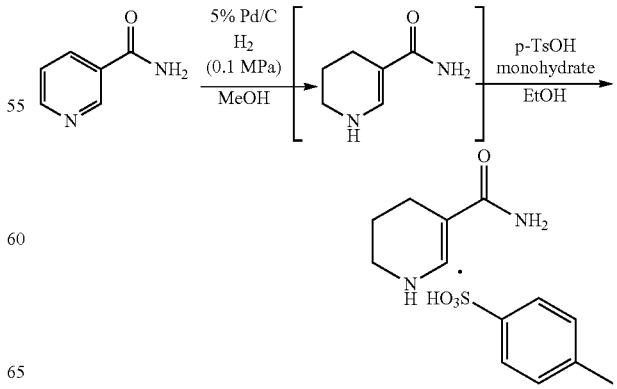

Nicotinamide (50.00 g) [mw. 122.12, 0.409 mol], 5% Pd/C (5.00 g) and methanol (500 mL) were placed in an autoclave (1 L), and the nicotinamide was dissolved. The system was purged with hydrogen gas, and the hydrogen pressure was raised to 0.10 MPa. The mixture was warmed to 40° C., and stirred for 20 hr under constant hydrogen pressure (0.1 MPa) at the rotation speed of 350 rpm. After the system was freed from pressure, the Pd/C was removed by filtration on hot through membrane filter (0.5 μm). The filtrate was concentrated under reduced pressure, to the residue (powder) was added was added methanol (100 mL), and the mixture was stirred for 1 hr in ice bath. The crystals were collected by filtration under reduced pressure, and washed with cooled methanol (30 mL). To the obtained wet crystals (38.44 g) was added ethanol (308 mL), and p-toluenesulfonic acid monohydrate (63.75 g) [mw, 190.22, 0.335 mol] was added thereto, and dissolved. The mixture was aged at room temperature for 3.5 hr, and the crystals were collected by filtration under reduced pressure, washed with ethanol (100 mL), and dried at 50° C. under reduced pressure to give the desired compound. White crystalline powder, 84.09 g, yield 68%.

$^1$H-NMR (500 MHz, D$_2$O) δ(ppm) 1.72-1.76 (m, 2H), 2.15 (t, J=6.31 Hz, 2H), 3.05-3.15 (m, 2H), 7.38 (s, 1H).

(The protons derived from NH, OH and COOH was not detected)

$^{13}$C-NMR (125 MHz, D$_2$O) δ(ppm) 20.03, 39.75, 94.15, 143.62, 173.99.

Anal. Calcd for C$_6$H$_{10}$N$_2$O: C, 57.12; H, 7.99; N, 22.21. Found: C, 57.11; H, 8.09; N, 22.10.

ESI-MS: m/z 127.0873 [M±H]$^+$.

IR (ATR, cm$^{-1}$):3300 (νNH), 3201 (νNH), 3000-2800 (νCH), 1622 (νC=O), 1506 (νC=C), 1423 (δCH), 1362 (δCH).

Reference Example 2

Synthesis of ditrifluoroacetato[(S)-(−)-2,2'-bis(diphenylphosphino)-1,1'-binaphthyl]ruthenium(II) Complex

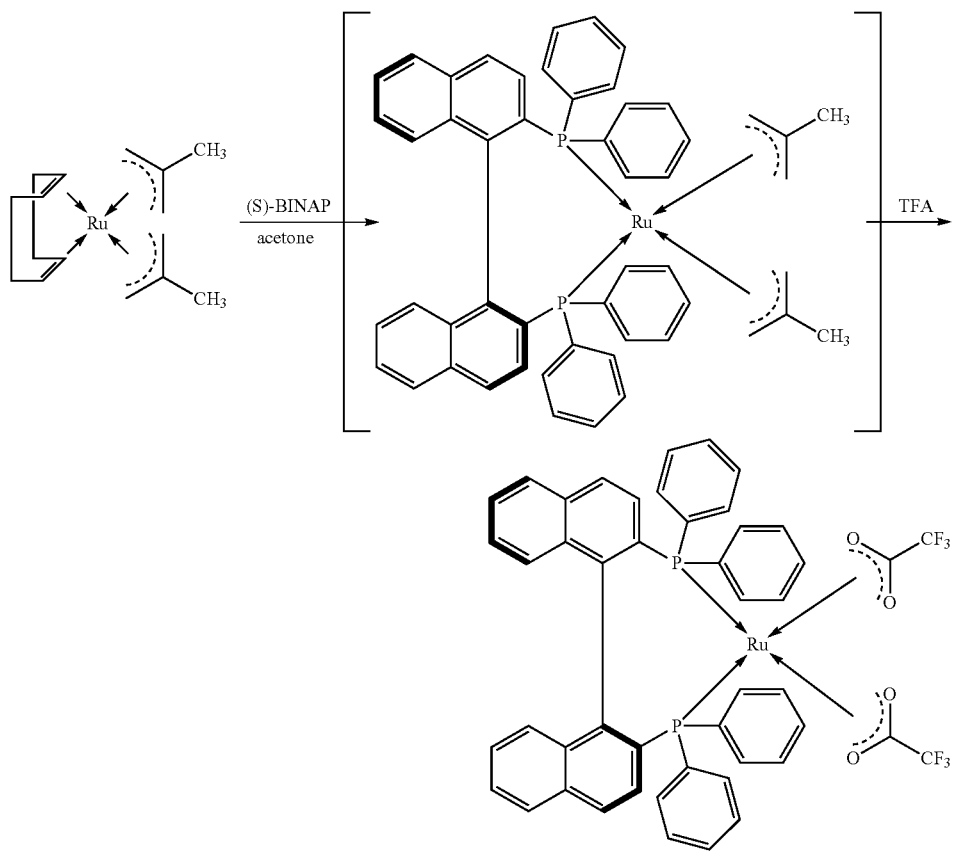

Bis(2-methylallyl)(1,5-cyclooctadiene)ruthenium(II) (6.29 g) [mw. 319.45, 19.69 mmol] and (S)-2,2'-bis(diphenylphosphino)-1,1'-binaphthyl (12.51 g) [mw. 622.69, 20.09 mmol, 1.02 eq.] were placed in Schlenk flask, and the system was purged seven times with argon. Acetone (253 g, dehydrated for organic synthesis) was added thereto, and the mixture was stirred in the range of 20 to 30° C. for 1 hr. Trifluoroacetic acid (3 mL) [d=1.535, mw. 114.02, 40.4 mmol] was added thereto in the range of 20 to 30° C., and the mixture was stirred in the range of 30 to 35° C. for 24 hr. The reaction solution was concentrated under reduced pressure at 40° C. or lower until the distillation was completed, and to the residue was added n-hexane (250 mL, dehydrated for organic synthesis). The mixture was heated to the range of 35 to 45° C., and stirred for 2 hr. After solid-liquid separation, the wet substance was washed with n-hexane (50 mL, dehydrated for organic synthesis), and dried at 50° C. under reduced pressure to give the desired compound. Pale-brown powder, 16.96 g, yield 91%.

¹H-NMR (500 MHz, CDCl₃, TMS) δ (ppm) 6.35-6.40 (m, 2H), 6.55 (br, 4H), 6.68 (br, 2H), 6.88 (br, 2H), 7.11 (br, 4H), 7.30 (br, 2H), 7.44 (br, 4H), 7.52 (br, 2H), 7.68 (br, 8H), 7.88 (br, 2H).
¹⁹F-NMR (471 MHz, CDCl₃, TFA) δ (ppm) −76.88 (s).
³¹P-NMR (202 MHz, CDCl₃, H₃PO₄) δ (ppm) 56.46 (s).

Example 2

Synthesis of ditrifluoroacetato[(S)-(−)-2,2'-bis(bis(4-chlorophenyl)phosphino)-1,1'-binaphthyl]ruthenium (II) Complex

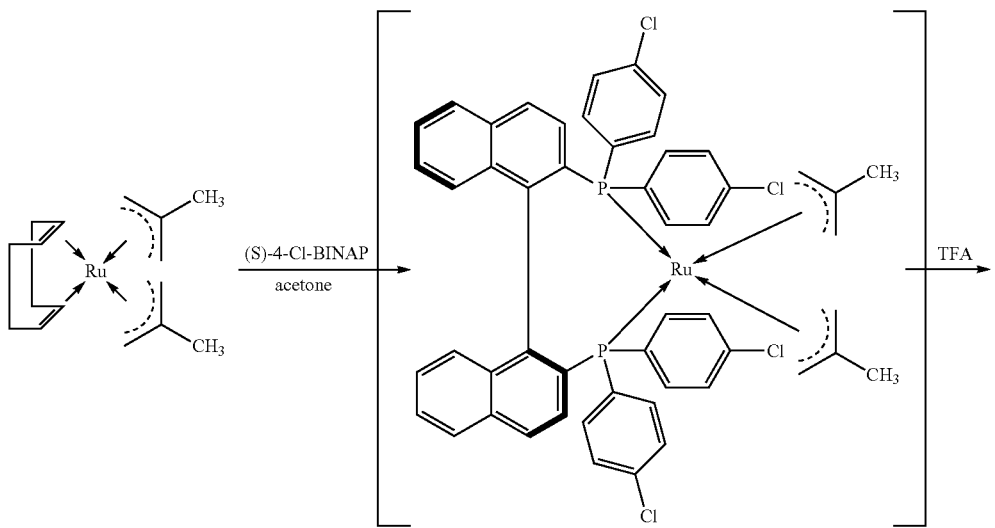

Bis(2-methylallyl)(1,5-cyclooctadiene)ruthenium(II) (0.112 g) [mw. 319.45, 0.350 mmol] and (S)-2,2'-bis(bis(4-chlorophenylphosphino)-1,1'-binaphthyl (0.293 g) [mw. 760.45, 0.385 mmol] were placed in Schlenk flask, and the system was purged seven times with argon. Dehydrated acetone (6 mL) was added thereto, and the mixture was stirred at room temperature for 15 min. Trifluoroacetic acid (0.053 mL) [d=1.535, mw. 114.02, 0.718 mmol] was added thereto at room temperature, and the mixture was stirred at room temperature for 22 hr. The reaction solution was concentrated under reduced pressure at 40° C. or lower until the distillation was completed, and to the residue was added dehydrated n-hexane (10 mL). The mixture was heated to 40° C., and stirred for 15 min. After solid-liquid separation, the wet substance was washed with dehydrated n-hexane (10 mL), and dried at 50° C. under reduced pressure to give the desired compound. Yellow powder.

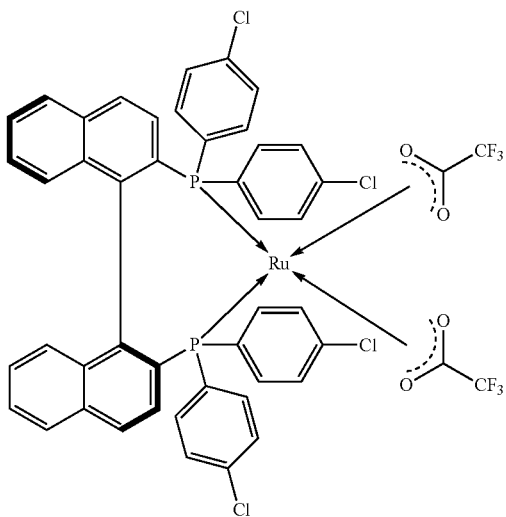

¹H-NMR (500 MHz, CD₃OD, TMS) δ (ppm) 6.25-6.36 (m, 2H), 6.40-6.55 (m, 4H), 6.84-7.03 (m, 6H), 7.28-7.39 (m, 2H), 7.41-7.52 (m, 4H), 7.62-7.75 (m, 6H), 7.76-7.89 (m, 4H).
³¹P-NMR (202 MHz, CD₃OD, H₃PO₄) δ (ppm) 55.42 (s).

Example 3

Synthesis of ditrifluoroacetato[(R_P,R'_P)-1,1'-bis[(S)-α-(dimethylamino)benzyl]-2,2'-bis(diphenylphosphino)ferrocene]ruthenium(II) Complex

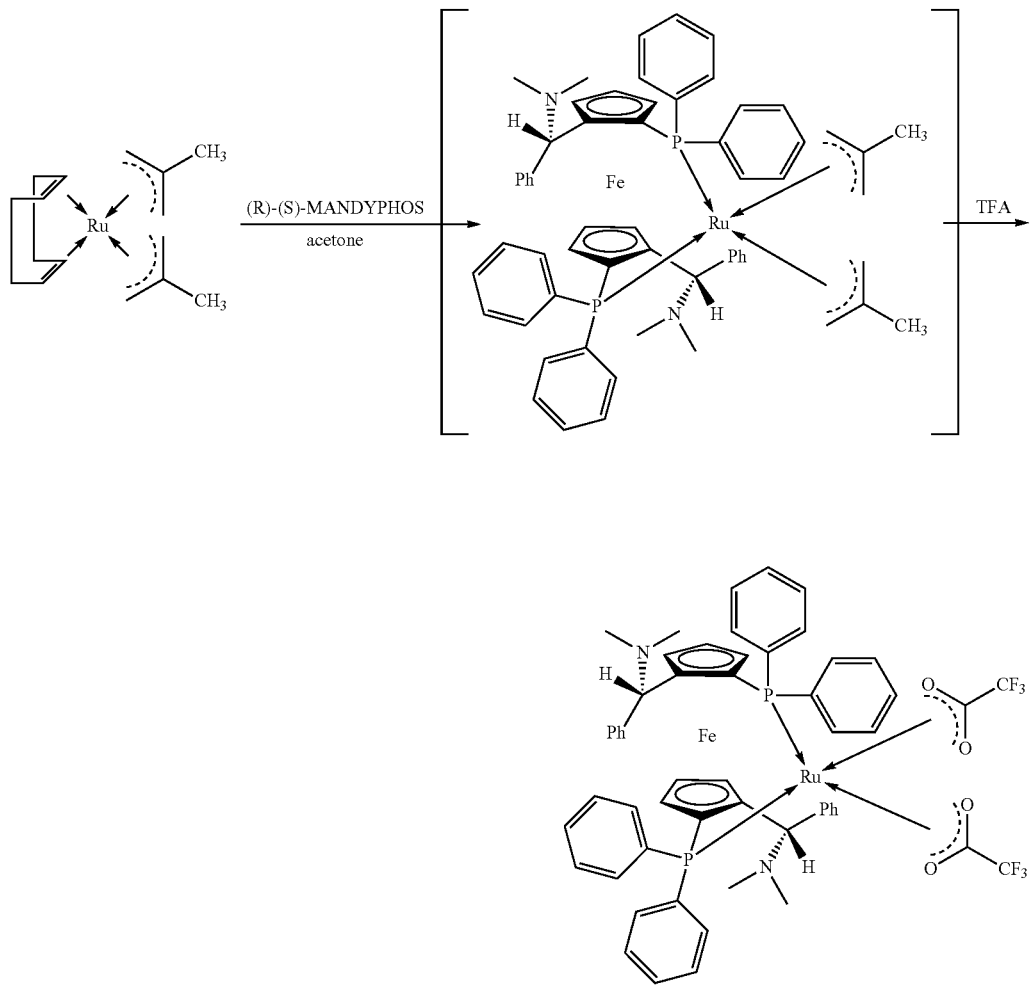

Bis(2-methylallyl)(1,5-cyclooctadiene)ruthenium(II) (0.112 g) [mw. 319.45, 0.350 mmol] and (R_P,R'_P)-1,1'-bis[(S)-α-(dimethylamino)benzyl]-2,2'-bis(diphenylphosphino)ferrocene (0.316 g) [mw. 820.76, 0.385 mmol] were placed in Schlenk flask, and the system was purged five times with argon. Dehydrated acetone (6 mL) was added thereto, and the mixture was stirred at room temperature for 15 min. Trifluoroacetic acid (0.053 mL) [d=1.535, mw. 114.02, 0.718 mmol] was added thereto at room temperature, and the mixture was stirred at room temperature for 22 hr. The reaction solution was concentrated under reduced pressure at 40° C. or lower until the distillation was completed, and to the residue was added dehydrated n-hexane (10 mL). The mixture was heated to 40° C., and stirred for 15 min. After solid-liquid separation, the wet substance was washed with dehydrated n-hexane (10 mL), and dried at 50° C. under reduced pressure to give the desired compound. Yellow powder.

$^{31}$P-NMR (202 MHz, CD$_3$OD, H$_3$PO$_4$) δ (ppm) 63.14 (s).

Example 4

Synthesis of (R)-piperidine-3-carboxamide p-toluenesulfonate (Step 1) Synthesis of crude (R)-piperidine-3-carboxamide p-toluenesulfonate

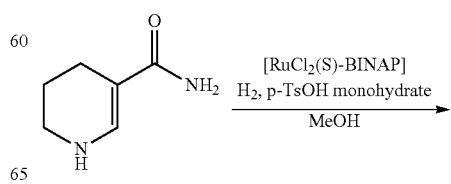

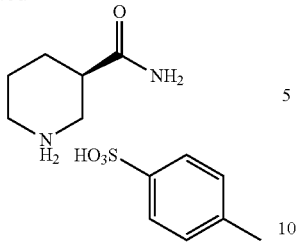

RuCl₂{(S)-binap} (63.0 mg) [mw. 794.67, 0.0793 mmol], 1,4,5,6-tetrahydropyridine-3-carboxamide (5.00 g) [mw. 126.16, 39.63 mmol] and p-toluenesulfonic acid monohydrate (8.29 g) [mw. 190.20, 43.59 mmol] were placed in an autoclave (300 mL), and the system was purged seven times with argon. Dehydrated methanol (100 mL) for organic synthesis was added thereto by argon pressure. The system was purged ten times with hydrogen gas, and pressurized to 1.15 MPa, and the mixture was stirred at the internal temperature of 65° C. (the external temperature 75° C.) for 18 hr. After the system was freed from hydrogen pressure, the mixture was concentrated under reduced pressure, and to the residue was added ethyl acetate (50 mL). The mixture was aged at room temperature for 1 hr, and filtered under reduced pressure, and the substance collected by filtration was washed with ethyl acetate (appropriate amount), and dried at 50° C. under reduced pressure to give the desired compound. Pale-yellow white crystalline powder, 10.86 g, yield 91%, optical purity 75% ee.

¹H-NMR (500 MHz, D₂O) δ(ppm) 1.55-1.72 (m, 2H), 1.76-1.97 (m, 2H), 2.29 (s, 3H), 2.65-2.76 (m, 1H), 2.88-2.99 (m, 1H), 3.00-3.07 (m, 1H), 3.12-3.22 (m, 1H), 3.22-3.29 (m, 1H), 7.27 (d, J=7.88 Hz, 2H), 7.62 (d, J=7.88 Hz, 2H). (The protons derived from NH, OH and COOH was not detected)

¹³C-NMR (125 MHz, D₂O) δ(ppm) 20.58, 25.57, 38.42, 43.93, 44.77, 125.45, 129.55, 139.74, 142.48, 177.26.

Anal. Calcd for C₁₃H₂₀N₂O₄S: C, 51.98; H, 6.71; N, 9.33; S, 10.68. Found: C, 51.20; H, 6.73; N, 9.02; S, 11.14.

ESI-MS: m/z 129.1033 (C₆H₁₂N₂O)[M+H]⁺, m/z 171.0135(C₇H₈O₃S)[M−H]⁻.

IR (ATR, cm⁻¹):3163 (νNH), 2900-2800(νCH), 1670 (νC=O), 1435 (δCH), 1170 (νS=O).

(high-performance liquid chromatography conditions)
column: CD-Ph (manufactured by Shiseido)
mobile phase: 0.1 mol/L-aqueous hexafluoropotassium phosphate
solution/acetonitrile (volume ratio: 95/5)
flow rate: 0.5 mL/min
detection: UV 200 nm
temperature: 25° C.
retention time: (S)-form 15.2 min, (R)-form 17.0 min.

(Step 2) Purification of (R)-piperidine-3-carboxamide p toluenesulfonate

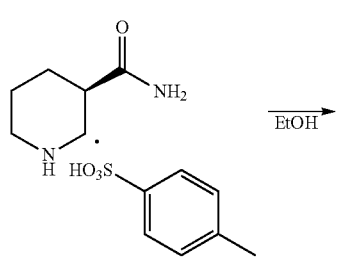

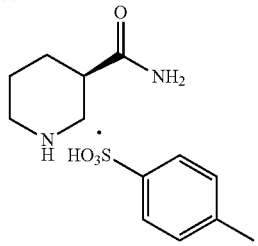

The crude (R)-piperidine-3-carboxamide p-toluenesulfonate obtained in Step 1 (103.57 g) [mw. 300.37, 0.3448 mol] and ethanol (311 mL) were placed in a four-necked flask (1 L). The internal temperature was raised to 65° C., and the crude material was completely dissolved. The mixture was stirred at the same temperature for 15 min, and allowed to cool at air. At the time that the internal temperature was cooled to 55° C., the seed crystals of the desired compound were added thereto. The crystallization started slowly, and the mixture was aged at 25° C. for 1 hr. The mixture was filtered under reduced pressure, and the substance collected by filtration was washed with ethanol (207 mL), and dried at 60° C. under reduced pressure to give the desired compound. White crystalline powder, 50.27 g, yield 49%, optical purity>99% ee.

¹H-NMR (500 MHz, D₂O) δ(ppm) 1.55-1.71 (m, 2H), 1.76-1.87 (m, 1H), 1.86-1.96 (m, 1H), 2.28 (s, 3H), 2.65-2.75 (m, 1H), 2.88-2.99 (m, 1H), 3.00-3.07 (m, 1H), 3.12-3.22 (m, 1H), 3.22-3.29 (m, 1H), 7.26 (d, J=8.20 Hz, 2H), 7.60 (d, J=8.51 Hz, 2H).

¹³C-NMR (125 MHz, D₂O) δ(ppm) 20.55, 25.55, 38.39, 43.89, 44.72, 125.42, 129.51, 139.64, 142.47, 177.28.

Anal. Calcd for C₁₃H₂₀N₂O₄S: C, 51.98; H, 6.71; N, 9.33; S, 10.68. Found: C, 51.90; H, 6.79; N, 9.24; S, 10.65.

ESI-MS: m/z 129.1035 (C₆H₁₂N₂O)[M+H]⁺, m/z 171.0134 (C₇H₈O₃S)

IR(ATR, cm⁻¹):3159 (νNH), 2950-2800(νCH), 1670 (νC=O), 1435 (δCH), 1171 (νS=O).

[α] (c 0.98, MeOH, 25° C.)=−0.45°.

(high-performance liquid chromatography conditions)
column: CD-Ph (manufactured by Shiseido)
mobile phase: 0.1 mol/L-aqueous hexafluoropotassium phosphate
solution/acetonitrile (volume ratio: 95/5)
flow rate: 0.5 mL/min
detection: UV 200 nm
temperature: 25° C.
retention time: (S)-form 15.2 min, (R)-form 17.0 min.

Example 5

Synthesis of (R)-piperidine-3-carboxamide p-toluenesulfonate

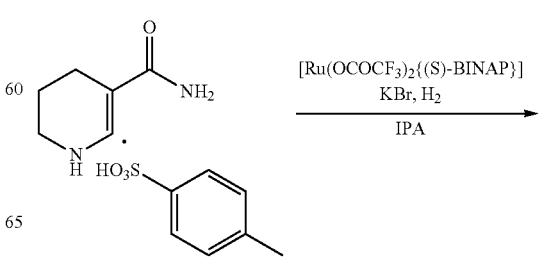

-continued

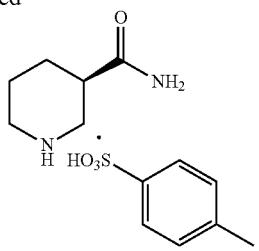

Ditrifluoroacetato[(S)-(−)-2,2'-bis(diphenylphosphino)-1,1'-binaphthyl]ruthenium(II) complex (95.0 mg) [mw. 949.77, 0.100 mmol], 5-carbamoyl-1,2,3,4-tetrahydropyridin-1-ium 4-methylbenzenesulfonate (1,4,5,6-tetrahydropyridine-3-carboxamide p-toluenesulfonate) (67.51 g) [mw. 337.53 (0.85 ethanolate), 0.200 mol] and potassium bromide (119.0 mg) [mw. 119.00, 1.000 mmol] were placed in an autoclave (1 L), and the system was purged seven times with argon. Dehydration 2-propanol (500 mL) for organic synthesis was added thereto by argon pressure. The system was purged ten times with hydrogen gas, and pressurized to 0.80 MPa, and the internal temperature was raised to 50° C. Then, the hydrogen pressure was raised to 1.00 MPa, and the mixture was stirred under constant pressure (1.00 MPa) at the internal temperature of 50° C. for 48 hr. The system was freed from hydrogen pressure (rotation speed 800 rpm), and purged with nitrogen gas, and the nitrogen gas was raised to 0.15 MPa, and the mixture was stirred at 50° C. for 15 min (100% conversion, optical purity 61% ee). The system was freed from nitrogen pressure, and the mixture was concentrated under reduced pressure. To the residue (powder) was added ethanol (100 mL), and the mixture was concentrated under reduced pressure. Again, to the residue (powder) was added ethanol (100 mL), and the mixture was concentrated under reduced pressure. To the residue (powder) was added ethanol (180 mL), and the residue was dissolved at 70° C., and the solution was stirred at the same temperature for 10 min. The solution was cooled to 25° C. over 30 min. In the process of cooling (at 60° C.), the seed crystals of the desired compound were added thereto. The mixture was aged for 2 hr, and filtered under reduced pressure. The substance collected by filtration was washed with ethanol (100 mL), and dried at 60° C. under reduced pressure to give the desired compound. White crystalline powder, 38.95 g, yield 65%, optical purity>99% ee.

(high-performance liquid chromatography conditions)
column: CD-Ph (manufactured by Shiseido)
mobile phase: 0.1 mol/L aqueous hexafluoropotassium phosphate solution/acetonitrile (volume ratio: 95/5)
flow rate: 0.5 mL/min
detection: UV 200 nm
temperature: 25° C.
retention time: (S)-form 15.2 min, (R)-form 17.0 min.

Example 6

Synthesis of (R)-piperidine-3-carboxamide p-toluenesulfonate

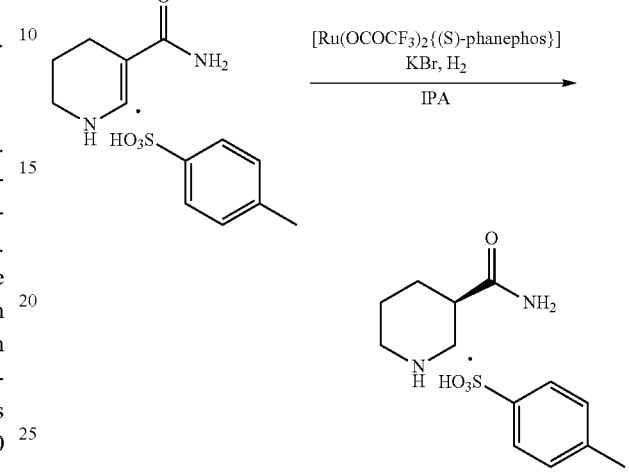

Ditrifluoroacetato[(S)-(+)-4,12-bis(diphenylphosphino)-[2,2]-paracyclophane]ruthenium(II) complex (3.6 mg) [mw. 949.77, 0.0379 mmol], 5-carbamoyl-1,2,3,4-tetrahydropyridin-1-ium 4-methylbenzenesulfonate (1,4,5,6-tetrahydropyridine-3-carboxamide p-toluenesulfonate) (2.675 g) [mw. 337.53 (0.85 ethanolate), 7.926 mmol] and potassium bromide (4.7 mg) [mw. 119.00, 0.0396 mmol] were placed in an autoclave (120 mL), and the system was purged seven times with argon. Dehydrated 2-propanol (20 mL) for organic synthesis was added thereto by argon pressure. The system was purged ten times with hydrogen gas, the hydrogen pressure was raised to 1.0 MPa, and the mixture was stirred under constant pressure (1.00 MPa) at the internal temperature of 50° C. for 62 hr (100% conversion, optical purity 84% ee). The system was freed from hydrogen pressure, and the mixture was concentrated under reduced pressure. To the residue (powder) was added ethanol (5 mL), and the mixture was concentrated under reduced pressure. Again, to the residue (powder) was added ethanol (5 mL), and the mixture was concentrated under reduced pressure. To the residue (powder) was added ethanol (8 mL), the residue was dissolved at 85° C., and the solution was cooled to 25° C., aged for 2 hr, and filtered under reduced pressure. The substance collected by filtration was washed with ethanol (6 mL), and dried at 60° C. under reduced pressure to give the desired compound. White crystalline powder, 1.813 g, yield 76%, optical purity>99% ee.

(high-performance liquid chromatography conditions)
column: CD-Ph (manufactured by Shiseido)
mobile phase: 0.1 mol/L-aqueous hexafluoropotassium phosphate solution/acetonitrile (volume ratio: 95/5)
flow rate: 0.5 mL/min
detection: UV 200 nm
temperature: 25° C.
retention time: (S)-form 15.2 min, (R)-form 17.0 min.

Example 7

Synthesis of (R)-piperidine-3-carboxamide p-toluenesulfonate

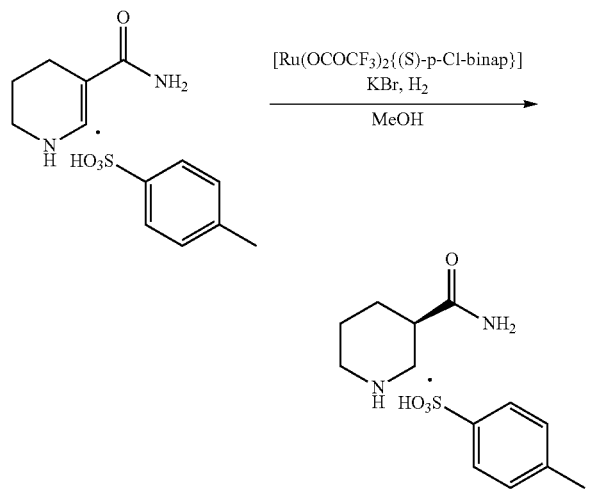

Ditrifluoroacetato[(S)-(−)-2,2'-bis(bis(4-chlorophenyl)phosphino)-1,1'-binaphthyl]ruthenium(II) complex (8.6 mg) [mw. 1087.55, 0.0079 mmol], 5-carbamoyl-1,2,3,4-tetrahydropyridin-1-ium 4-methylbenzenesulfonate (1,4,5,6-tetrahydropyridine-3-carboxamide p-toluenesulfonate) (2.675 g) [mw. 337.53 (0.85 ethanolate), 7.926 mmol] and potassium bromide (9.4 mg) [mw. 119.00, 0.0792 mmol] were placed in an autoclave (120 mL), and the system was purged seven times with argon. Dehydrated methanol (20 mL) for organic synthesis was added thereto by argon pressure. The system was purged ten times with hydrogen gas, the hydrogen pressure was raised to 1.0 MPa, and the mixture was stirred under constant pressure (1.00 MPa) at the internal temperature of 50° C. for 21 hr. To measure optical purity, 0.2 mL of the reaction solution was then taken, the amine moiety was benzoylated with benzoyl chloride and triethylamine, and the optical purity was measured (100% conversion, optical purity 77% ee). The system was freed from hydrogen pressure, and the mixture was concentrated under reduced pressure. To the residue was added ethanol (7.2 mL), and the residue was dissolved at 90° C., and the solution was cooled to 25° C., aged for 2 hr, and filtered under reduced pressure. The substance collected by filtration was washed with ethanol (6 mL), and dried at 60° C. under reduced pressure to give the desired compound. White crystalline powder, 1.4441 g, yield 61%, optical purity>99% ee.

(high-performance liquid chromatography conditions)
column: IC (manufactured by Daicel)
mobile phase: 0.020 mol/L-aqueous phosphoric acid solution/acetonitrile (volume ratio: 7/3)
flow rate: 0.5 mL/min
detection: UV 200 nm
temperature: 25° C.
retention time: (R)-form 12.6 min, (S)-form 16.4 min.

Example 8

Synthesis of (R)-piperidine-3-carboxamide p-toluenesulfonate

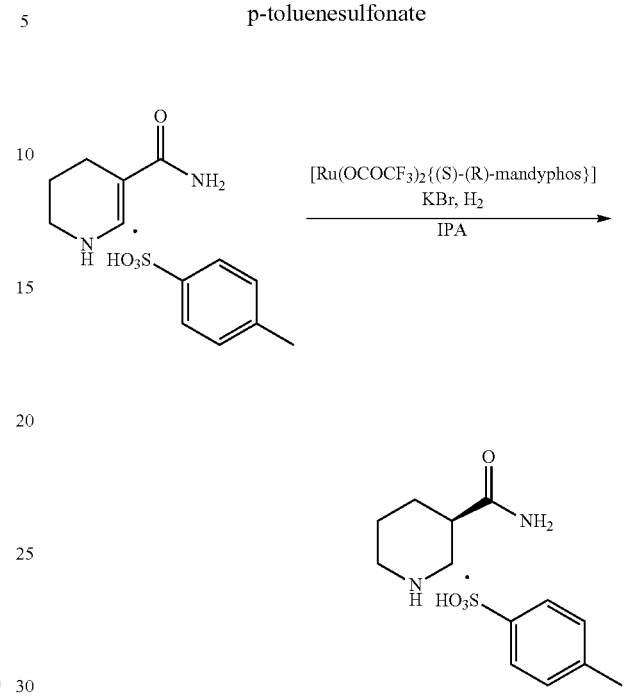

Ditrifluoroacetato[($R_P$,$R'_P$)-bis[(S)-α-(dimethylamino)benzyl]-2,2'-bis(diphenylphosphino)ferrocene]ruthenium (II) complex (9.1 mg) [mw. 1147.86, 0.0079 mmol], 5-carbamoyl-1,2,3,4-tetrahydropyridin-1-ium 4-methylbenzenesulfonate (1,4,5,6-tetrahydropyridine-3-carboxamide p-toluenesulfonate) (2.675 g) [mw. 337.53 (0.85 ethanolate), 7.926 mmol] and potassium bromide (9.4 mg) [mw. 119.00, 0.0792 mmol] were placed in an autoclave (120 mL), and the system was purged seven times with argon. Dehydrated 2-propanol (20 mL) for organic synthesis was added thereto by argon pressure. The system was purged ten times with hydrogen gas, the hydrogen pressure was raised to 1.0 MPa, and the mixture was stirred under constant pressure (1.00 MPa) at the internal temperature of 50° C. for 14 hr (100% conversion, optical purity 96% ee). The system was freed from hydrogen pressure, and the mixture was concentrated under reduced pressure. To the residue was added ethanol (4.8 mL), and the residue was dissolved at 90° C., and the solution was cooled to 25° C., aged for 2 hr, and filtered under reduced pressure. The substance collected by filtration was washed with ethanol (6 mL), and dried at 60° C. under reduced pressure to give the desired compound. White crystalline powder, 2.001 g, yield 84%, optical purity>99% ee.

(high-performance liquid chromatography conditions)
column: CD-Ph (manufactured by Shiseido)
mobile phase: 0.1 mol/L-aqueous hexafluoropotassium phosphate solution/acetonitrile (volume ratio: 95/5)
flow rate: 0.5 mL/min
detection: UV 200 nm
temperature: 25° C.
retention time: (S)-form 15.2 min, (R)-form 17.0 min.

57
Example 9

Synthesis of (R)-piperidine-3-carboxamide p-toluenesulfonate

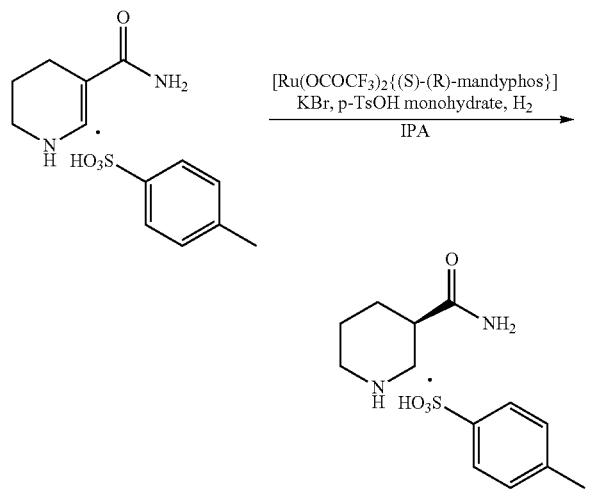

Ditrifluoroacetato[(R$_P$,R'$_P$)-1,1'-bis[(S)-α-(dimethylamino)benzyl]-2,2'-bis(diphenylphosphino)ferrocene]ruthenium(II) complex (5.5 mg) [mw. 1147.86, 0.0048 mmol], 5-carbamoyl-1,2,3,4-tetrahydropyridin-1-ium 4-methylbenzenesulfonate (1,4,5,6-tetrahydropyridine-3-carboxamide p-toluenesulfonate) (3.38 g) [mw. 337.53 (0.85 ethanolate), 10.01 mmol], potassium bromide (6.0 mg) [mw. 119.00, 0.050 mmol] and p-toluenesulfonic acid monohydrate (0.19 g) [mw. 190.22, 1.00 mmol] were placed in an autoclave (120 mL), and the system was purged seven times with argon. Degassed and dehydrated 2-propanol (25 mL) for organic synthesis was added thereto by argon pressure, and the mixture was stirred for 2 hr at approximately room temperature. The system was purged ten times with hydrogen gas, and pressurized to 0.90 MPa, and the mixture was stirred at the internal temperature of 50° C. for 20 hr, cooled to about 5° C., and stirred at the same temperature for 3 hr. The system was freed from hydrogen pressure, and the crystals were collected by filtration under reduced pressure, and washed with 2-propanol (5 mL), and dried at 60° C. under reduced pressure to give the desired compound. White crystalline powder, 2.71 g, yield 90%, optical purity>99.9% ee.

(high-performance liquid chromatography conditions)
column: CHIRALPAK AD-H (manufactured by Daicel)
mobile phase: a mixed solvent of n-heptane/ethanol/methanol/diethylamine (volume ratio: 800/150/50/1)
flow rate: 0.8 mL/min
detection: UV 220 nm
temperature: 40° C.
retention time: (S)-form 11.3 min, (R)-form 12.2 min.

58
Example 10

Synthesis of crude (R)-piperidine-3-carboxamide p-toluenesulfonate

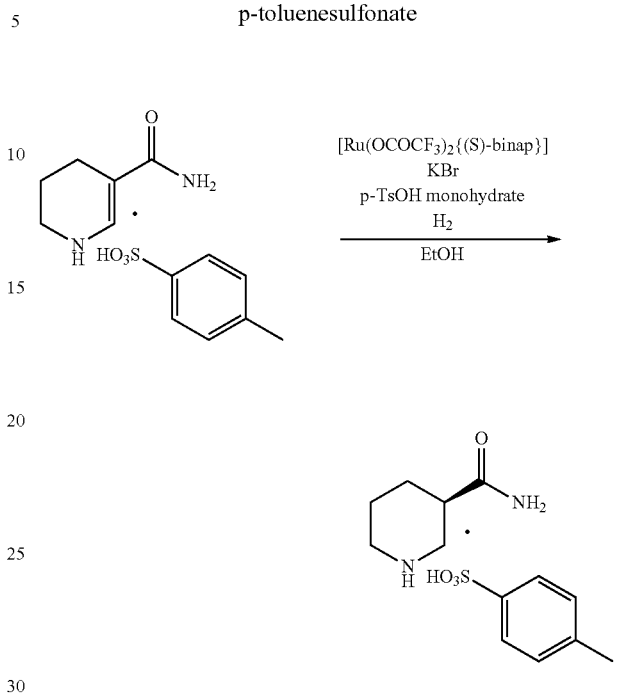

Ditrifluoroacetato[(S)-(−)-2,2'-bis(diphenylphosphino)-1,1'-binaphthyl]ruthenium(II) complex (4.6 mg) [mw. 949.77, 0.0048 mmol], 5-carbamoyl-1,2,3,4-tetrahydropyridin-1-ium 4-methylbenzenesulfonate (1,4,5,6-tetrahydropyridine-3-carboxamide p-toluenesulfonate) (3.38 g) [mw. 337.53 (0.85 ethanolate), 10.01 mmol], potassium bromide (6.1 mg) [mw. 119.00, 0.0513 mmol] and p-toluenesulfonic acid monohydrate (0.19 g) [mw. 190.22, 1.00 mmol] were placed in an autoclave (120 mL), and the system was purged seven times with argon. Degassed and dehydrated ethanol (25 mL) for organic synthesis was added thereto by argon pressure, and the mixture was stirred for 2 hr at approximately room temperature. The system was purged ten times with hydrogen gas, and pressurized to 0.90 MPa, and the mixture was stirred under constant hydrogen pressure (0.90 MPa) at the internal temperature of 50° C. for 20 hr, cooled to about 5° C., and stirred at the same temperature for 39 hr. The system was freed from hydrogen pressure, and the crystals were collected by filtration under reduced pressure, washed with ethanol (5 mL), and dried at 60° C. under so reduced pressure to give the desired compound. White crystalline powder, 1.91 g, yield 64%, optical purity 98.2% ee.

(high-performance liquid chromatography conditions)
column: CHIRALPAK AD-H (manufactured by Daicel)
mobile phase: a mixed solvent of n-heptane/ethanol/methanol/diethylamine (volume ratio: 800/150/50/1)
flow rate: 0.8 mL/min
detection: UV 220 nm
temperature: 40° C.
retention time: (S)-form 11.3 min, (R)-form 12.2 min.

Example 11

Synthesis of (R)-piperidine-3-carboxamide p-toluenesulfonate (Step 1) Synthesis of crude (R)-piperidine-3-carboxamide p-toluenesulfonate

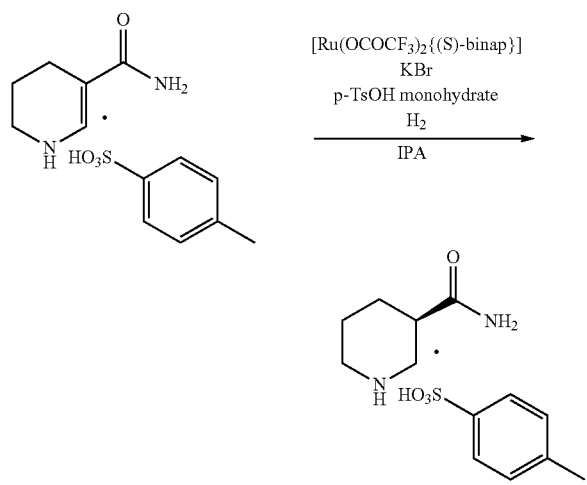

Ditrifluoroacetato[(S)-(−)-2,2'-bis(diphenylphosphino)-1,1'-binaphthyl]ruthenium(II) complex (95.1 mg) [mw. 949.77, 0.100 mmol], 5-carbamoyl-1,2,3,4-tetrahydropyridin-1-ium 4-methylbenzenesulfonate (1,4,5,6-tetrahydropyridine-3-carboxamide p-toluenesulfonate) (67.60 g) [mw. 337.53 (0.85 ethanolate), 200.3 mmol], potassium bromide (119.2 mg) [mw. 119.00, 1.00 mmol] and p-toluenesulfonic acid monohydrate (3.80 g) [mw. 190.22, 20.0 mmol] were placed in an autoclave (1 L), and the system was purged seven times with argon. Degassed and dehydrated 2-propanol (500 mL) for organic synthesis was added thereto by argon pressure, and the mixture was stirred for 2 hr at approximately room temperature. The system was purged ten times with hydrogen gas, and pressurized to 0.90 MPa, and the mixture was stirred under constant hydrogen pressure (0.90 MPa) at the internal temperature of 50° C. for 20 hr, cooled to about 5° C., and stirred at the same temperature for 3 hr. The system was freed from hydrogen pressure, and the crystals were collected by filtration under reduced pressure, and washed with 2-propanol (100 mL), and dried at 60° C. under reduced pressure to give the desired compound. White crystalline powder, 56.00 g, yield 93%, optical purity 70% ee.

(high-performance liquid chromatography conditions)
column: CHIRALPAK AD-H (manufactured by Daicel)
mobile phase: a mixed solvent of n-heptane/ethanol/methanol/diethylamine (volume ratio: 800/150/50/1)
flow rate: 0.8 mL/min
detection: UV 220 nm
temperature: 40° C.
retention time: (S)-form 11.3 min, (R)-form 12.2 min.

(Step 2) Purification of (R)-piperidine-3-carboxamide p-toluenesulfonate

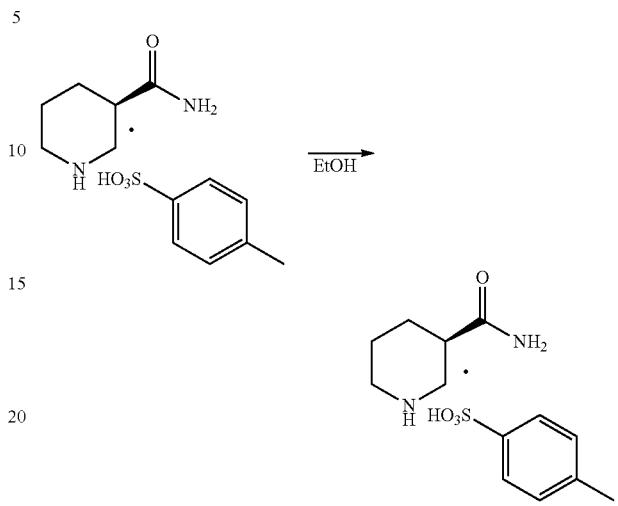

The crude (R)-piperidine-3-carboxamide p-toluenesulfonate obtained in Step 1 (55.00 g) [mw. 300.37, 183.1 mmol] and ethanol (440 mL) were placed in a four-necked flask (1 L). The internal temperature was raised to 78° C., and the crude material was completely dissolved. The solution was stirred at the same temperature for 30 min, and allowed to cool under air. At the time that the internal temperature was cooled to 60° C., the seed crystals (55 mg) of the desired compound were added thereto. The crystallization started slowly, and the mixture was aged at 25° C. for 11 hr. The mixture was filtered under reduced pressure, and the substance collected by filtration was washed with 2-propanol (83 mL), and dried at 60° C. under reduced pressure to give the desired compound. White crystalline powder, 38.60 g, yield 70%, optical purity 99.7% ee.

(high-performance liquid chromatography conditions)
column: CHIRALPAK AD-H (manufactured by Daicel)
mobile phase: a mixed solvent of n-heptane/ethanol/methanol/diethylamine (volume ratio: 800/150/50/1)
flow rate: 0.8 mL/min
detection: UV 220 nm
temperature: 40° C.
retention time: (S)-form 11.3 min, (R)-form 12.2 min.

Example 12

Synthesis of (R)-1-(3-(2-cyanobenzyl)-1-methyl-2,6-dioxo-1,2,3,6-tetrahydropyrimidin-4-yl)piperidine-3-carboxamide

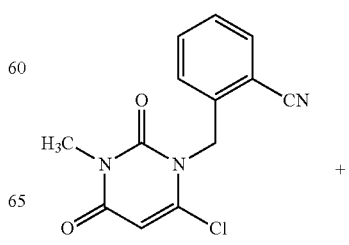

+

-continued

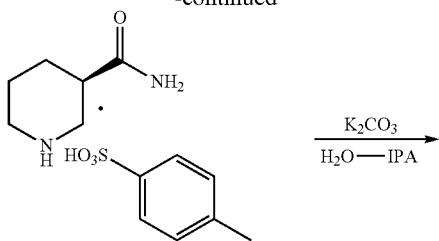

(R)-Piperidine-3-carboxamide p-toluenesulfonate (20.00 g) [mw. 300.37, 66.58 mmol], 2-((6-chloro-3-methyl-2,4-dioxo-3,4-dihydropyrimidin-1(2H)-yl)methyl)benzonitrile (18.20 g) [mw. 275.69, 66.02 mmol] and potassium carbonate (18.20 g) [mw. 138.21, 131.7 mmol] were placed in a four-necked flask (1 L), and isopropanol (15 mL) and water (40 mL) were added thereto. The mixture was stirred at internal temperature of 65° C. for 23 hr, and water (120 mL) was added thereto. The mixture was cooled to 0° C., aged for 2 hr, and filtered under reduced pressure, and the substance collected by filtration was washed with water (50 mL), and dried at 60° C. under reduced pressure to give the desired compound. White crystalline powder, 22.97 g, yield 95%.

$^1$H-NMR (500 MHz, CDCl$_3$, TMS) δ(ppm) 1.46 (qt, J=13.0, 3.5 Hz, 1H), 1.70 (dt, J=13.5, 4.0 Hz, 1H), 1.91 (dd, J=13.0, 3.5 Hz, 1H), 2.47 (tt, J=11.5, 3.5 Hz, 1H), 2.55 (t, J=11.5 Hz, 1H), 2.72 (t, J=11.5 Hz, 1H), 2.88 (d, J=11.5 Hz, 1H), 3.12-3.20 (dm, 1H), 3.25 (s, 3H), 5.13 (d, J=16.0 Hz, 1H), 5.32 (d, J=16.0 Hz, 1H), 5.34 (s, 1H), 5.67 (bs, 1H), 5.73 (bs, 1H), 7.11 (d, J=8.0 Hz, 1H), 7.32 (t, J=7.5 Hz, 1H), 7.51 (td, J=8.0, 1.5 Hz, 1H), 7.61 (dd, J=7.5, 1.5 Hz, 1H).

$^{13}$C-NMR (125 MHz, CDCl$_3$, CDCl$_3$) δ(ppm) 24.28, 27.30, 28.20, 42.46, 46.43, 51.91, 54.01, 91.27, 110.74, 117.68, 127.18, 128.18, 133.28, 133.61, 141.01, 152.99, 159.80, 163.01, 174.80.

ESI-MS: m/z 368.1731[M+H]$^-$, 390.1557[M+Na]$^+$, 406.1262 [M+H]$^+$.

IR(ATR, cm$^{-1}$):3387, 3319, 3202 (vNH), 2941, 2853 (vCH), 2226 (vCN), 1690, 1676, 1628 (δCH).

[α] (c 0.98, MeOH, 25° C.)=−21.4°.

Example 13

Synthesis of (R)-2-((6-(3-aminopiperidin-1-yl)-3-methyl-2,4-dioxo-3,4-dihydropyrimidin-1(2H)-yl)methyl)benzonitrile

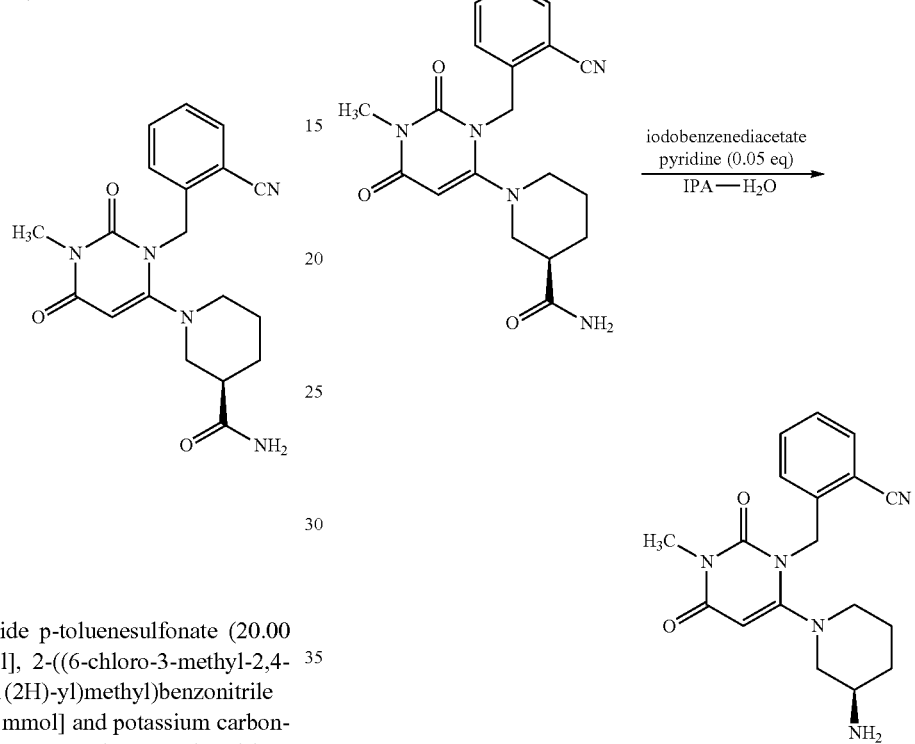

A mixture (1.5 L) of water and isopropanol (1/1(v/v)) was placed in a four-necked flask (2 L), pyridine (550 μL) [d=0.98, mw. 79.10, 6.9 mmol] and (R)-1-(3-(2-cyanobenzyl)-1-methyl-2,6-dioxo-1,2,3,6-tetrahydropyrimidin-4-yl)piperidine-3-carboxamide (50.0 g) [mw. 367.40, 136 mmol] were added successively thereto. Then, iodobenzene diacetate (48.2 g) [mw. 322.10, 150 mmol] was added thereto, and the mixture was stirred 20° C. for 3 hr. The volatile was evaporated using evaporator under reduced pressure, and the residual aqueous solution was washed with ethyl acetate (500 mL, twice). The solution was cooled to about 0° C., potassium carbonate (400 g) was added thereto in several parts at 15° C. or lower, and the mixture was extracted with toluene (100 mL) and isopropanol (150 mL). After separation, the organic layer was washed with saturated brine (50 mL), and concentrated using evaporator under reduced pressure. To the residue was added toluene (150 mL), and the mixture was concentrated under reduced pressure. The residue was suspended in toluene (100 mL), n-heptane (150 mL) was added thereto, and the mixture was aged at room temperature for 3 hr, and filtered under reduced pressure. The substance collected by filtration was washed with a mixed solvent of toluene/n-heptane (2v/3v, 50 mL), and dried at 50° C. under reduced pressure to give the desired compound. Pale-yellow white crystalline powder, 40.3 g, yield 87%.

Reference Example 3

Synthesis of (R)-2-((6-(3-aminopiperidin-1-yl)-3-methyl-2,4-dioxo-3,4-dihydropyrimidin-1(2H)-yl)methyl)benzonitrile benzoate

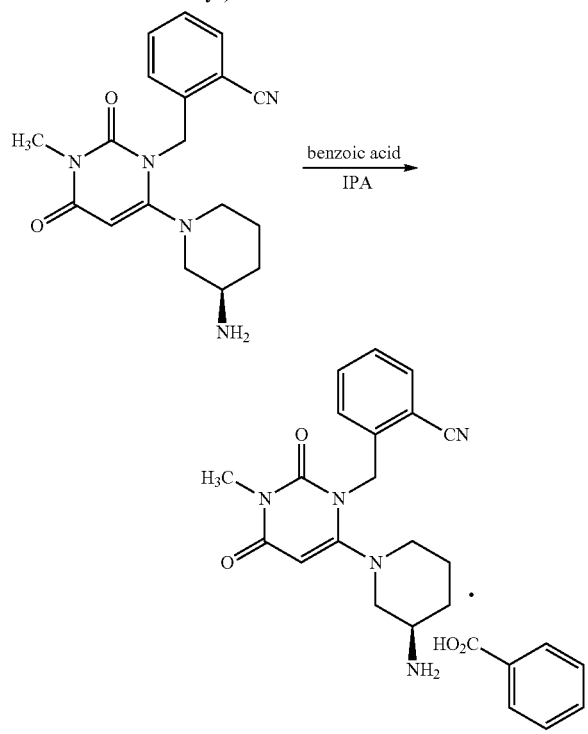

(R)-2-((6-(3-Aminopiperidin-1-yl)-3-methyl-2,4-dioxo-3,4-dihydropyrimidin-1(2H)-yl)methyl)benzonitrile (35.0 g) [mw. 339.39, 103 mmol] and isopropanol (140 mL) were placed in an round bottom flask (300 mL). The mixture was heated at 60° C. to dissolve the material, and a solution prepared by dissolving benzoic acid (13.8 g) [mw. 122.12, 113 mmol] in ethyl acetate (140 mL) was added dropwise thereto at the same temperature. The mixture was aged at room temperature for 18 hr, and filtered under reduced pressure. The substance collected by filtration was washed successively with a mixed solvent of isopropanol/ethyl acetate (1v/1v, 150 mL) and ethyl acetate (50 mL), and dried at 50° C. under reduced pressure to give the desired compound. Pale-yellow white crystalline powder, 43.9 g, yield 92%.

Example 14

Synthesis of (R)-1-(3-(2-cyano-5-fluorobenzyl)-1-methyl-2,6-dioxo-1,2,3,6-tetrahydropyrimidin-4-yl)piperidine-3-carboxamide

(R)-Piperidine-3-carboxamide p-toluenesulfonate (5.00 g) [mw. 300.37, 16.65 mmol], 2-((6-chloro-3-methyl-2,4-dioxo-3,4-dihydropyrimidin-1(2H)-yl)methyl)-4-fluorobenzonitrile (4.90 g) [mw. 293.68, 16.68 mmol] and potassium carbonate (4.60 g) [mw. 138.21, 33.3 mmol] were placed in an round-bottom flask (50 mL), and isopropanol (7.5 mL) and water (20 mL) were added thereto. The mixture was stirred at the internal temperature of 65° C. for 24 hr, and cooled to room temperature. Water (30 mL) was added thereto, and the mixture was stirred at 0° C. for 1 hr. The precipitate was filtered under reduced pressure, and the substance collected by filtration was washed with water (10 mL), dried at 45° C. under reduced pressure to give the desired compound. White crystalline powder, 5.6 g, yield 87%.

$^1$H-NMR (500 MHz, CDCl$_3$) δ (ppm) 1.45-1.60 (m, 1H) 1.62-1.72 (m, 1H) 1.80 (m, 1H) 1.92-2.07 (m, 1H) 2.49-2.59 (m, 1H) 2.64 (t, J=10.88 Hz, 1H) 2.82 (t, J=10.56 Hz, 1H) 2.94 (d, J=11.98 Hz, 1H) 3.14-3.28 (m, 1H) 3.34 (s, 3H) 5.17 (d, J=16.39 Hz, 1H) 5.38 (d, 1H, J=16.08 Hz, 1H) 5.42 (s, 1H) 5.48 (brs, 1H) 5.66 (brs, 1H) 6.90 (dd, J=9.14 Hz, 2.52 Hz, 1H) 7.10 (td, J=8.04 Hz, 2.52 Hz, 1H) 7.70 (dd, J=8.67 Hz, 5.20 Hz, 1H).

Example 15

Synthesis of (R)-2-((6-(3-aminopiperidin-1-yl)-3-methyl-2,4-dioxo-3,4-dihydropyrimidin-1(2H)-yl)methyl)-4-fluorobenzonitrile

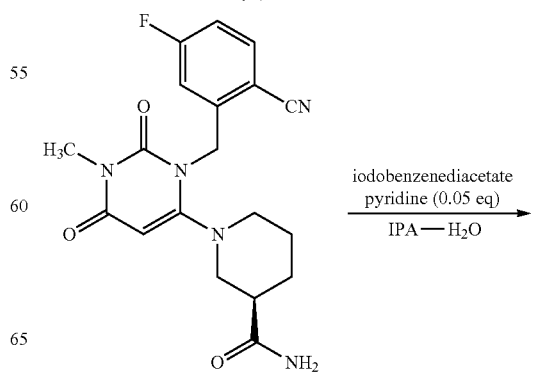

-continued

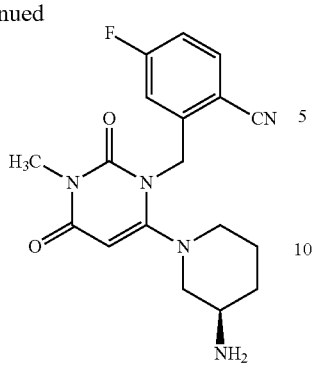

A mixture (60 mL) of water and isopropanol (1/1(v/v)) was placed in a four-necked flask (100 mL), and pyridine (21.4 μL) [d=0.98, mw. 79.10, 0.26 mmol] and (R)-1-(3-(2-cyano-5-fluorobenzyl)-1-methyl-2,6-dioxo-1,2,3,6-tetrahydropyrimidin-4-yl)piperidine-3-carboxamide (2.00 g) [mw. 385.39, 5.19 mmol] were successively added thereto. Then, iodobenzene diacetate (1.84 g) [mw. 322.10, 5.71 mmol] was added thereto, and the mixture was stirred at 20° C. for 3 hr. The volatile was evaporated using evaporator under reduced pressure, and the residual aqueous solution was washed with ethyl acetate (20 mL, twice). The solution was cooled to about 0° C., potassium carbonate (16 g) was added thereto in several parts at 15° C. or lower, and the mixture was extracted with toluene (6 mL) and isopropanol (6 mL). After separation, the organic layer was washed with saturated brine (10 mL), and concentrated using evaporator under reduced pressure. To the residue was added toluene (6 mL), and the mixture was concentrated under reduced pressure. The residue was suspended in toluene (6 mL), n-heptane (6 mL) was added thereto, and the mixture was aged at 0° C. for 1 hr, and filtered under reduced pressure. The substance collected by filtration was dried at 50° C. under reduced pressure to give the desired compound. White crystalline powder, 1.6 g, yield 86%.

$^1$H-NMR (500 MHz, CDCl$_3$) δ (ppm) 1.23 (d, J=11.03 Hz, 1H) 1.30 (brs, 2H) 1.56-1.67 (m, 1H) 1.72-1.83 (m, 1H) 1.95 (dd, J=12.77 Hz, 3.94 Hz, 1H) 2.41 (m, 1H) 2.61 (m, 1H) 2.87-2.98 (m, 2H) 2.99-3.05 (m, 1H) 3.32 (s, 3H) 5.23-5.32 (m, 2H) 5.39 (s, 1H) 6.86 (dd, J=8.99 Hz, 2.36 Hz, 1H) 7.09 (td, J=8.04 Hz, 2.52 Hz, 1H) 7.69 (dd, J=8.51 Hz, 5.36 Hz, 1H).

$^{13}$C NMR (126 MHz, CDCl$_3$) δppm 28.0, 33.4, 46.1, 51.9, 59.7, 90.8, 114.6, 114.7, 115.6, 115.8, 116.4, 135.4, 135.5, 144.6, 152.7, 159.5, 162.9.

Reference Example 4

Synthesis of (R)-2-((6-(3-aminopiperidin-1-yl)-3-methyl-2,4-dioxo-3,4-dihydropyrimidin-1(2H)-yl)methyl)-4-fluorobenzonitrile Succinate

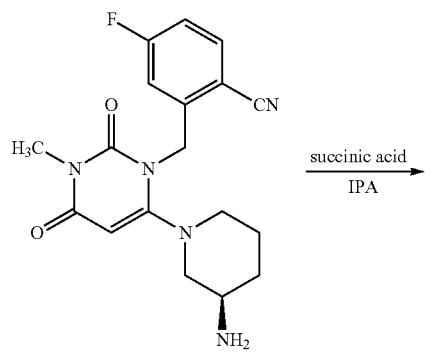

-continued

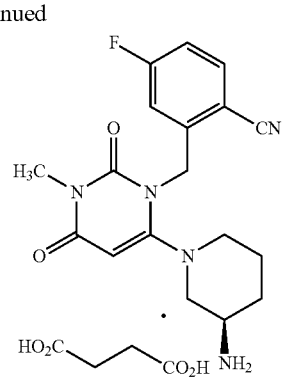

(R)-2-((6-(3-Aminopiperidin-1-yl)-3-methyl-2,4-dioxo-3,4-dihydropyrimidin-1(2H)-yl)methyl)-4-fluorobenzonitrile (1.0 g) [mw. 357.38, 2.8 mmol], tetrahydrofuran (4.5 mL) and water (two drops) were placed in an round-bottom flask (50 mL). The mixture was heated at 65° C. to dissolve the material, and a solution prepared by dissolving succinic acid (0.331 g) [mw. 118.09, 2.8 mmol] in tetrahydrofuran (4 mL) and isopropanol (2.5 mL) was added dropwise thereto at the same temperature. The mixture was stirred at 65° C. for 30 min, aged at room temperature for 16 hr, and stirred at 0° C. for 2 hr. The precipitate was collected by filtration under reduced pressure, and dried at 45° C. under reduced pressure to give the desired compound. White crystalline powder, 1.2 g, yield 93%.

$^1$H-NMR (500 MHz, DMSO) δ (ppm) 1.35 (d, J=8.83 Hz, 1H) 1.42-1.57 (m, 1H) 1.66-1.97 (m, 2H) 2.54-2.77 (m, 2H) 2.91 (d, J=11.35 Hz, 1H) 3.00-3.07 (m, 1H) 3.08 (m, 1H) 3.09 (s, 3H) 3.14 (m, 1H) 5.12 (d, J=16.08 Hz, 1H) 5.20 (d, J=16.39 Hz, 1H) 5.38 (s, 1H) 7.17 (dd, J=9.62 Hz, 2.36 Hz, 1H) 7.35 (td, J=8.51 Hz, 2.52 Hz, 1H) 7.95 (dd, J=8.67 Hz, 5.52 Hz, 1H).

$^{13}$C NMR (126 MHz, DMSO) δ ppm 27.9, 31.6, 46.3, 47.0, 51.7, 55.8, 90.3, 106.9, 115.7, 117.1, 136.45, 136.53, 145.8, 152.3, 159.7, 162.7, 164.1, 166.1, 175.2.

Example 16

Synthesis of (R)-2-((6-(3-aminopiperidin-1-yl)-3-methyl-2,4-dioxo-3,4-dihydropyrimidin-1(2H)-yl)methyl)benzonitrile benzoate

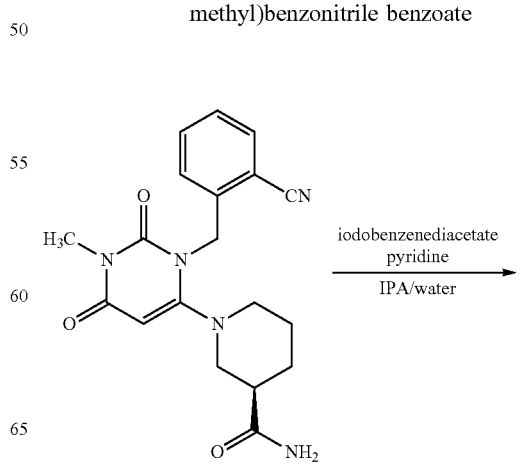

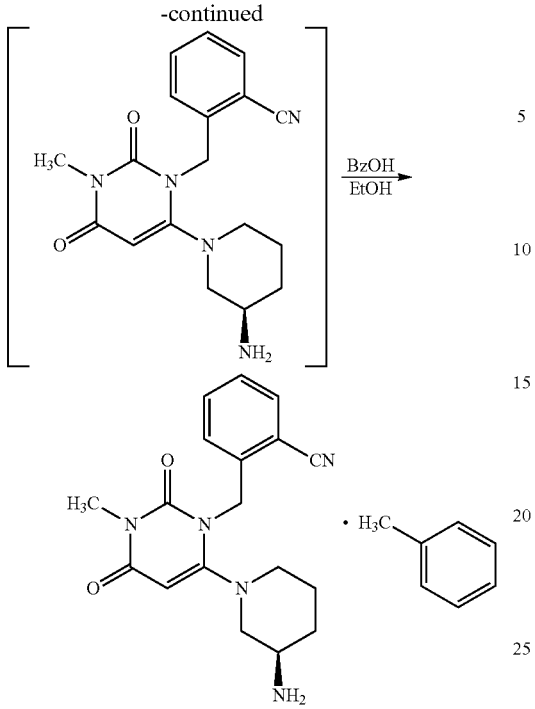

A mixture (1250 mL) of water and isopropanol (1/1(v/v)) was placed in a four-necked flask (2 L), and pyridine (495 µL) [d=0.98, mw. 79.10, 6.2 mmol] and (R)-1-(3-(2-cyanobenzyl)-1-methyl-2,6-dioxo-1,2,3,6-tetrahydropyrimidin-4-yl)piperidine-3-carboxamide (45.0 g) [mw. 367.40, 122 mmol] were successively added thereto. The mixture was cooled to 10° C. Then, iodobenzene diacetate (43.50 g) [mw. 322.10, 135 mmol] was added thereto, and the mixture was stirred at 10° C. for 5 hr. Ethyl acetate (450 mL) was added thereto, and the mixture was stirred. To the separated aqueous layer was added ethyl acetate (450 mL), and the mixture was stirred and separated. To the aqueous layer was added activated carbon (4.5 g), and the mixture was stirred for 30 min. The activated carbon was removed by filtration, and washed with water (45 mL). To the filtrate was added ethyl acetate (450 mL), and the mixture was cooled to 10° C. Potassium carbonate (270 g) was added thereto at 20° C. or lower, and the mixture was stirred for 30 min, and separated. To the obtained organic layer was added aqueous sodium chloride solution (prepared by dissolving sodium chloride (24 g) in water (80 mL)), and the mixture was stirred, and separated. The organic layer was concentrated to about 135 mL under reduced pressure. To the residue was added ethanol (180 mL), and the mixture was concentrated to about 135 mL under reduced pressure. The residue was filtered through membrane filter (0.2 micron) to remove the insoluble substances, and washed with ethanol (32 mL). The filtrate was heated to 70° C., and benzoic acid ethanol solution (prepared by dissolving benzoic acid (14.90 g) [mw. 122.21, 122 mmol] in ethanol (90 mL)) was added dropwise thereto over 30 min in the range of 70 to 73° C. The mixture was gradually cooled to 30° C. over 2 hr, and cooled to 0° C. The mixture was stirred at 0° C. for 2 hr, and the crystals were collected by filtration. The wet crystals were washed with cooled ethanol (90 mL), and dried at 60° C. under reduced pressure to give the desired compound. White crystalline powder, 46.79 g, yield 87%.

Example 17

Synthesis of (R)-2-((6-(3-aminopiperidin-1-yl)-3-methyl-2,4-dioxo-3,4-dihydropyrimidin-1(2H)-yl)methyl)benzonitrile benzoate

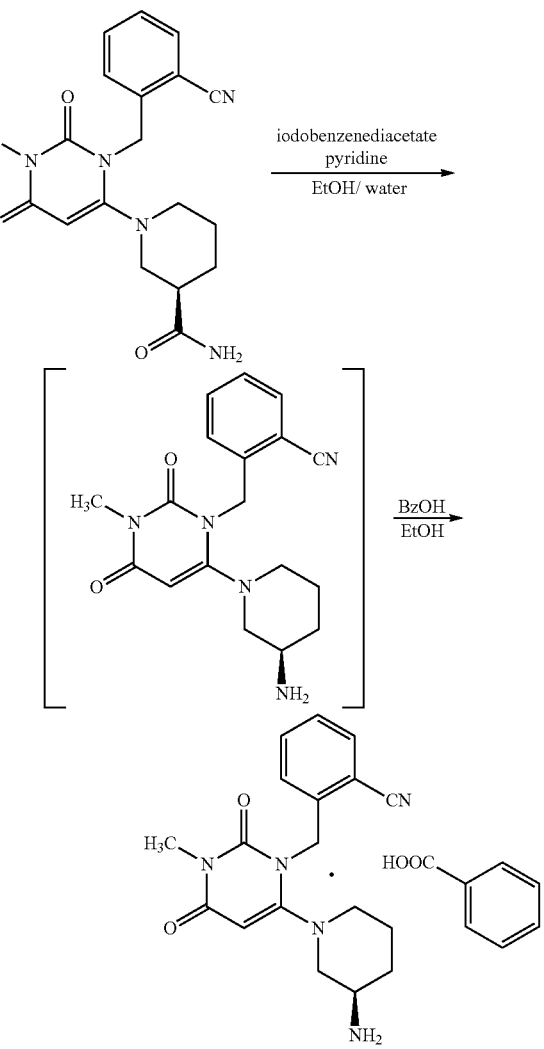

Ethanol (150 mL) and water (250 mL) were placed in a four-necked flask (500 mL), and pyridine (513 µL) [d=0.98, mw. 79.10, 6.36 mmol] and (R)-1-(3-(2-cyanobenzyl)-1-methyl-2,6-dioxo-1,2,3,6-tetrahydropyrimidin-4-yl)piperidine-3-carboxamide (50.0 g) [mw. 367.40, 136 mmol] were successively added thereto. Then, iodobenzene diacetate (48.23 g) [mw. 322.10, 150 mmol] was added thereto, and the mixture was stirred at 20° C. for 2 hr. After left standing, the iodobenzene of the lower layer was removed. The upper layer was concentrated to about 250 mL under reduced pressure, to the residue was added ethyl acetate (150 mL), and the mixture was stirred, and separated. To the lower layer was added ethyl acetate (150 mL), and the mixture was stirred, and separated. Ethyl acetate (150 mL) was added thereto, and the mixture was cooled to 10° C. Potassium carbonate (107 g) was added thereto at 20° C. or lower, and the mixture was stirred for 30 min, and separated. To the organic layer was added aqueous sodium chloride solution (prepared by dissolving sodium chloride (8 g) in water (30 mL)), sodium chloride (8 g) was added thereto, and the mixture was stirred, and separated. To the organic layer were added activated carbon (5 g) and ethanol (appropriate amount), and the mixture was stirred for 30 min. The activated carbon was removed by filtration, and the filtrate was concentrated to about 150 mL under reduced pressure. To the residue was added ethanol (150 mL), and the mixture was concentrated to about 150 mL under reduced pressure. To the residue was added ethanol (150 mL), and the mixture was concentrated to about 150 mL under reduced pressure. The residue was filtered through membrane filter (0.2 micron) to remove the insoluble substances, and washed with ethanol (40 mL). The filtrate was heated to 70° C., and benzoic acid ethanol solution (prepared by dissolving benzoic acid (16.62 g) [mw. 122.21, 136 mmol] in ethanol (100 mL)) was added dropwise thereto in the range of 70 to 73° C. over 30 min. The mixture was stirred at 70° C. for 1.5 hr, and gradually cooled to 30° C. over 2 hr, and cooled to 0° C. The mixture was stirred at 0° C. for 1 hr, and the crystals were collected by filtration. The wet crystals were washed with cooled ethanol (100 mL), and dried at 60° C. under reduced pressure to give the desired compound. Pale-yellow white crystalline powder, 44.03 g, yield 70%.

Example 18

Synthesis of (R)-piperidine-3-carboxamide p-toluenesulfonate

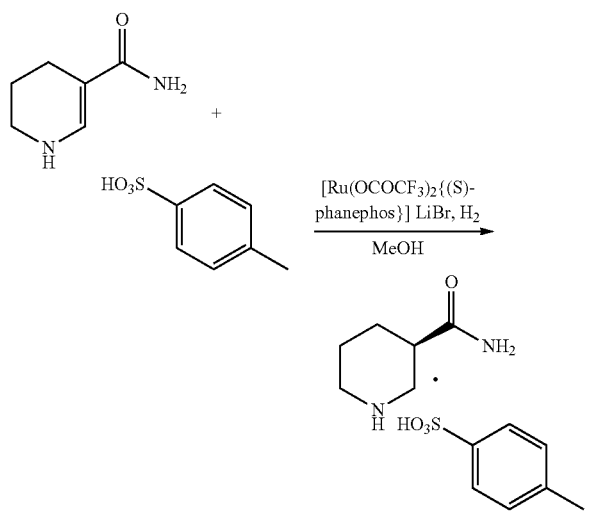

Ditrifluoroacetato[(S)-(+)-4,12-bis(diphenylphosphino)-[2,2]-paracyclophane]ruthenium(II) complex (7.1 mg) [mw. 903.72, 0.0079 mmol], 5-carbamoyl-1,2,3,4-tetrahydropyridine (1.00 g) [mw. 126.16, 7.926 mmol], p-toluenesulfonic acid monohydrate (1.508 g) [mw. 190.22, 7.926 mmol] and lithium bromide monohydrate (8.3 mg) [mw. 104.86, 0.0792 mmol] were placed in an autoclave (120 mL), and the system was purged seven times with argon. Dehydrated methanol (20 mL) for organic synthesis was added thereto by argon pressure. The system was purged ten times with hydrogen gas, the hydrogen pressure was raised to 1.0 MPa, and the mixture was stirred at the internal temperature of 50° C. for 15 hr. The system was freed from hydrogen pressure. To measure optical purity, 0.2 mL of the reaction solution was then taken, the amine moiety was benzoylated with benzoyl chloride and triethylamine, and the optical purity was measured (100% conversion, optical purity 87% ee). The mixture was concentrated under reduced pressure. To the residue (powder) was added ethanol (5 mL), and the mixture was concentrated under reduced pressure. Again, to the residue (powder) was added ethanol (5 mL), and the mixture was concentrated under reduced pressure. To the residue (powder) was added ethanol (7.4 mL), and the residue was dissolved at 80° C. The seed crystals of the desired compound were added thereto, and the mixture was cooled to 25° C., aged for 1 hr, and filtered under reduced pressure. The substance collected by filtration was washed with ethanol (6 mL), and dried at 60° C. under reduced pressure to give the desired compound. White crystalline powder, 1.813 g, yield 79%, optical purity>99% ee.

(high-performance liquid chromatography conditions)

column: IC (manufactured by Daicel)

mobile phase:

0.020 mol/L aqueous phosphoric acid solution/acetonitrile (volume ratio: 7/3)

flow rate: 0.5 mL/min detection: UV 200 nm temperature: 25° C.

retention time: (R)-form 12.6 min, (S)-form 16.4 min.

The reaction was performed by addition of the other additive instead of lithium bromide monohydrate, under the reaction conditions described in the above-mentioned Example. The results are shown below (the reaction solution was analyzed under the analysis conditions described in the above-mentioned Example, and concentration under reduced pressure and the treatments thereafter were not performed).

TABLE 1

| | | HPLC analysis result | | |
|---|---|---|---|---|
| Example | additive | reaction time | reaction yield | optical purity of product |
| Example 19 | TBAI[1] | 16 h | 100% | 83% ee |
| Example 20 | TBAB[2] | 16 h | 100% | 87% ee |
| Example 21 | TBAB[2] | 16 h | 100% | 84% ee |
| Example 22 | TBAC[3] | 18 h | 100% | 84% ee |
| Example 23 | n-butyl ammonium chloride | 16 h | 100% | 85% ee |
| Example 24 | LiCl | 18 h | 100% | 84% ee |
| Example 25 | KI | 15 h | 100% | 82% ee |

[1]tetrabutylammonium iodide
[2]tetraethylammonium bromide
[3]tetrabutylammonium chloride

Example 26

Synthesis of (R)-piperidine-3-carboxamide p-toluenesulfonate

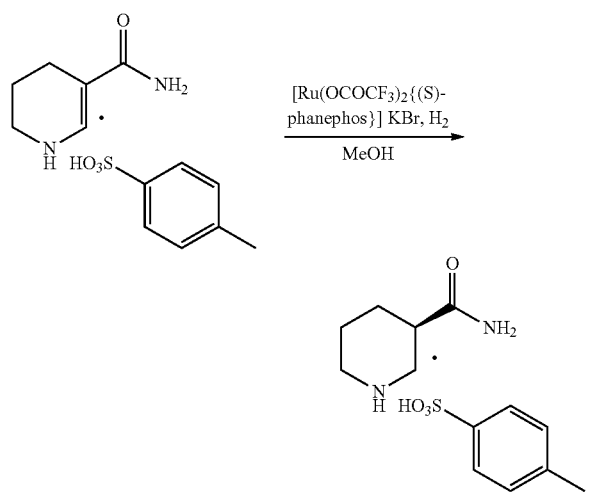

Ditrifluoroacetato[(S)-(+)-4,12-bis(diphenylphosphino)-[2,2]-paracyclophane]ruthenium(II) complex (7.1 mg) [mw. 903.72, 0.0079 mmol], 5-carbamoyl-1,2,3,4-tetrahydropyridin-1-ium 4-methylbenzenesulfonate (1,4,5,6-tetrahydropyridine-3-carboxamide p-toluenesulfonate) (2.675 g) [mw. 337.53 (0.85 ethanolate), 7.926 mmol] and potassium bromide (9.4 mg) [mw. 119.00, 0.0792 mmol] were placed in an autoclave (120 mL), and the system was purged seven times with argon. Dehydrated methanol (20 mL) for organic synthesis was added thereto by argon pressure. The system was purged ten times with hydrogen gas, the hydrogen pressure was raised to 1.0 MPa, and the mixture was stirred at the internal temperature of 50° C. for 17 hr. The system was freed from hydrogen pressure, the amine moiety was benzoylated by adding triethylamine and benzoyl chloride to 0.2 mL of the reaction solution, and the optical purity was measured (100% conversion, optical purity 88% ee). The mixture was concentrated under reduced pressure. To the residue (powder) was added ethanol, and the mixture was concentrated under reduced pressure. Again, to the residue (powder) was added ethanol, and the mixture was concentrated under reduced pressure. To the residue (powder) was added ethanol (7.4 mL), the solid was completely dissolved at 80° C., and the solution was cooled to 25° C. The mixture was aged at room temperature for 6 hr, and filtered under reduced pressure. The substance collected by filtration was washed with ethanol (6 mL), and dried at 60° C. under reduced pressure to give the desired compound. White crystalline powder, 1.74 g, yield 73%, optical purity>99% ee.

(high-performance liquid chromatography conditions)
column: IC (manufactured by Daicel)
mobile phase:
0.020 mol/L-aqueous phosphoric acid solution/acetonitrile (volume ratio: 7/3)
flow rate: 0.5 mL/min
detection: UV 200 nm
temperature: 25° C.
retention time: (R)-form 12.6 min, (S)-form 16.4 min.

The reaction was performed by addition of the other additive instead of potassium bromide, under the reaction conditions described in the above-mentioned Example. The results are shown below (the reaction solution was analyzed under the analysis conditions described in the above-mentioned Example, and concentration under reduced pressure and the treatments thereafter were not performed).

TABLE 2

| | | | HPLC analysis result | | |
|---|---|---|---|---|---|
| Example | additive | | reaction time | reaction yield | optical purity of product |
| Example 27 | LiBr monohydrate | | 17 h | 100% | 89% ee |
| Example 28 | TBAB[1)] | | 17 h | 100% | 88% ee |

[1)]tetraethylammonium bromide

Example 29

Synthesis of (R)-piperidine-3-carboxamide

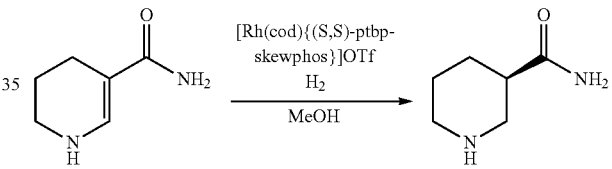

(2S,4S)-2,4-Bis[(di-4,4'-tert-butylphenyl)phosphino]pentanerhodium(I) trifluoromethanesulfonic acid complex (12.2 mg) [mw. 1025.08, 0.0119 mmol] and 5-carbamoyl-1,2,3,4-tetrahydropyridine (0.0300 g) [mw. 126.16, 0.238 mmol] were placed in a test tube equipped in hydrogenation apparatus with eight reactors (Endeavor (registered trademark)), the system was purged five times with argon, and dehydrated methanol (3.0 mL) for organic synthesis was added thereto using a syringe. The system was purged ten times with hydrogen gas, the hydrogen pressure was raised to 1.0 MPa, and the mixture was stirred at the internal temperature of 50° C. for 20 hr. The system was freed from hydrogen pressure. 2 mL of the reaction solution was then taken, and the amine moiety was benzyloxycarbonylated with triethylamine and benzyl chloroformate to give the desired compound.

(high-performance liquid chromatography conditions)
column: AD-RH (manufactured by Daicel)
mobile phase:
0.020 mol/L-aqueous phosphoric acid solution/acetonitrile (volume ratio: 7/3)
flow rate: 0.5 mL/min
detection: UV 220 nm
temperature: 25° C.
retention time: (S)-form 12.7 min, (R)-form 14.2 min.

Example 30

Synthesis of (R)-piperidine-3-carboxamide

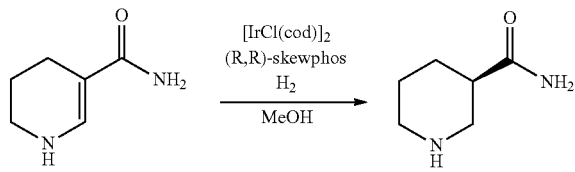 [SMILES: "MeOH" ; NC(=O)C1=CNCCC1 ; NC(=O)[C@@H]1CCCNC1]

[(1,5-Cyclooctadiene)iridium(I)]chloride dimer (4.0 mg) [mw. 671.71, 0.0119 mmol (iridium conversion)], (2R,4R)-2,4-bis[(diphenyl)phosphino]pentane (6.3 mg) [mw. 440.49, 0.0143 mmol] and 5-carbamoyl-1,2,3,4-tetrahydropyridine (0.0300 g) [mw. 126.16, 0.238 mmol] were placed in a test tube equipped in hydrogenation apparatus with eight reactors (Endeavor (registered trademark)), the system was purged five times with argon, and dehydrated methanol (3.0 mL) for organic synthesis was added thereto using a syringe. The system was purged ten times with hydrogen gas, the hydrogen pressure was raised to 1.0 MPa, and the mixture was stirred at the internal temperature of 50° C. for 20 hr. The system was freed from hydrogen pressure. 2 mL of the reaction solution was then taken, and the amine moiety was benzyloxycarbonylated with triethylamine and benzyl chloroformate to give the desired compound.

(high-performance liquid chromatography conditions)
column: AD-RH (manufactured by Daicel)
mobile phase:
0.020 mol/L-aqueous phosphoric acid solution/acetonitrile
(volume ratio: 7/3)
flow rate: 0.5 mL/min
detection: UV 220 nm
temperature: 25° C.
retention time: (S)-form 12.7 min, (R)-form 14.2 min.

Example 31

Synthesis of (S)-piperidine-3-carboxamide

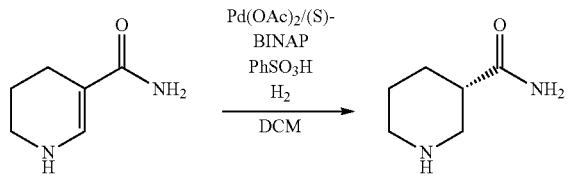

Palladium acetate (2.7 mg) [mw. 224.51, 0.0119 mmol], (S)-(−)-2,2'-bis(diphenylphosphino)-1,1'-binaphthyl (8.9 mg) [mw. 622.69, 0.0143 mmol], 5-carbamoyl-1,2,3,4-tetrahydropyridine (0.0300 g) [mw. 126.16, 0.238 mmol] and benzenesulfonic acid (37.6 mg) [mw. 158.18, 0.238 mmol] were placed in a test tube equipped in hydrogenation apparatus with eight reactors (Endeavor (registered trademark)), the system was purged five times with argon, and dehydrated dichloromethane (3.0 mL) for organic synthesis was added thereto using a syringe. The system was purged ten times with hydrogen gas, the hydrogen pressure was raised to 1.0 MPa, and the mixture was stirred at the internal temperature of 50° C. for 20 hr. The system was freed from hydrogen pressure. 2 mL of the reaction solution was then taken, and the amine moiety was benzyloxycarbonylated with triethylamine and benzyl chloroformate to give the desired compound.

(high-performance liquid chromatography conditions)
column: AD-RH (manufactured by Daicel)
mobile phase:
0.020 mol/L-aqueous phosphoric acid solution/acetonitrile (volume ratio: 7/3)
flow rate: 0.5 mL/min
detection: UV 220 nm
temperature: 25° C.
retention time: (S)-form 12.7 min, (R)-form 14.2 min.

INDUSTRIAL APPLICABILITY

According to the present invention, an optically active 6-(3-aminopiperidin-1-yl)-2,4-dioxo-1,2,3,4-tetrahydropyrimidine derivative can be efficiently produced, and therefore the present invention is useful for commercial production of a dipeptidylpeptidase inhibitor.

This application is based on patent application No. 2014-052809 filed on Mar. 14, 2014 in Japan, the contents of which are encompassed in full herein.

The invention claimed is:

1. A method of producing an optically active form of a compound represented by the formula:

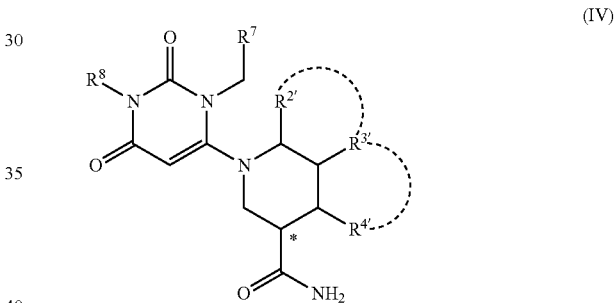

wherein
$R^{2'}$, $R^{3'}$ and $R^{4'}$ are independently a hydrogen atom, an optionally substituted hydrocarbon group, or an optionally substituted heterocyclic group; or
$R^{2'}$ and $R^{3'}$ in combination, or $R^{3'}$ and $R^{4'}$ in combination optionally form a 5- to 8-membered ring together with the adjacent atoms;
$R^7$ and $R^8$ are independently an optionally substituted hydrocarbon group, a hydrogen atom, or an optionally substituted heterocyclic group; and
the carbon atom marked with * is an asymmetric carbon atom,
or a salt thereof, which comprises reacting an optically active form of a compound represented by the formula:

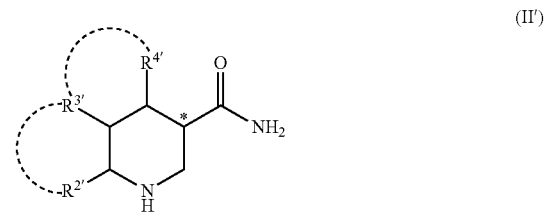

wherein each symbol is as defined above, or a salt thereof, with a compound represented by the formula:

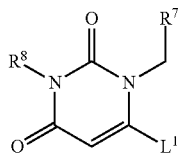

(III)

wherein
$L^1$ is a leaving group, and
the other symbols are as defined above,
or a salt thereof.

2. A method of producing an optically active form of a compound represented by the formula:

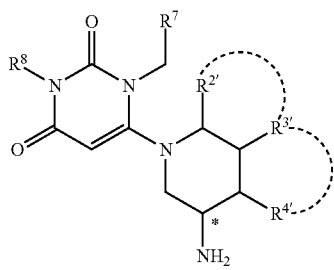

(V)

wherein
$R^{2'}$, $R^{3'}$ and $R^{4'}$ are independently a hydrogen atom, an optionally substituted hydrocarbon group, or an optionally substituted heterocyclic group, or
$R^{2'}$ and $R^{3'}$ in combination, or $R^{3'}$ and $R^{4'}$ in combination optionally form a 5- to 8-membered ring together with the adjacent atoms;
$R^7$ and $R^8$ are independently an optionally substituted hydrocarbon group, a hydrogen atom, or an optionally substituted heterocyclic group; and
the carbon atom marked with * is an asymmetric carbon atom,
or a salt thereof, which comprises subjecting an optically active form of a compound represented by the formula:

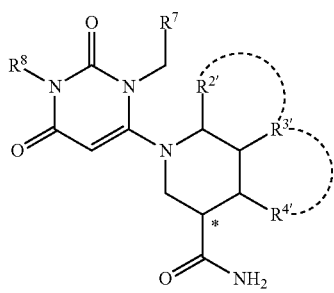

(IV)

wherein each symbol is as defined above,
or a salt thereof, to a rearrangement reaction.

3. The method according to claim 2, which further comprises (1) a step of subjecting a compound represented by the formula:

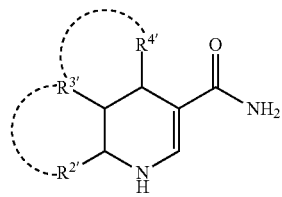

(I')

wherein each symbol is as defined in claim 2,
or a salt thereof, to a hydrogenation reaction in the presence of an organic metal complex to give an optically active form of a compound represented by the formula:

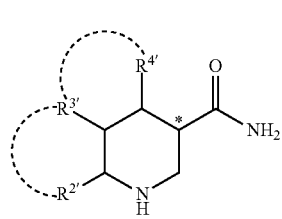

(II')

wherein each symbol is as defined in claim 2,
or a salt thereof; and (2) a step of reacting an optically active form of a compound represented by the formula:

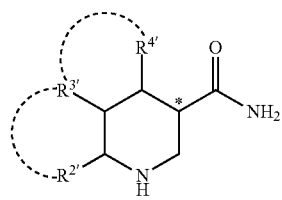

(II')

wherein each symbol is as defined above,
or a salt thereof, with a compound represented by the formula:

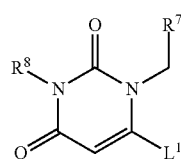

(III)

wherein
$L^1$ is a leaving group; and
the other symbols are as defined in claim 2,
or a salt thereof to give an optically active form of a compound represented by the formula:

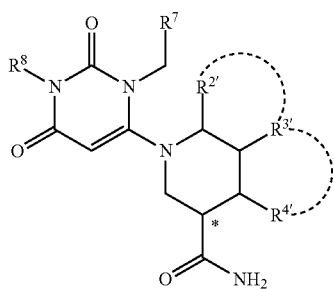

wherein each symbol is as defined above,
or a salt thereof.

4. A ruthenium complex represented by the formula:

$$[Ru(OCOR^{a\prime})_2 L^{a\prime}] \quad (VIII\prime)$$

wherein
$R^{a\prime}$ is a trifluoromethyl group; and
$L^{a\prime}$ is an optically active diphosphine ligand selected from
(1) an optically active form consisting of a compound represented by the formula:

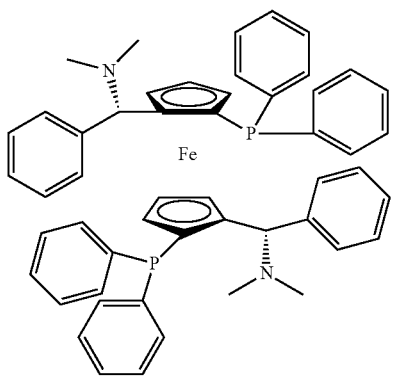

(Rp,S)- Mandyphos or
the formula:

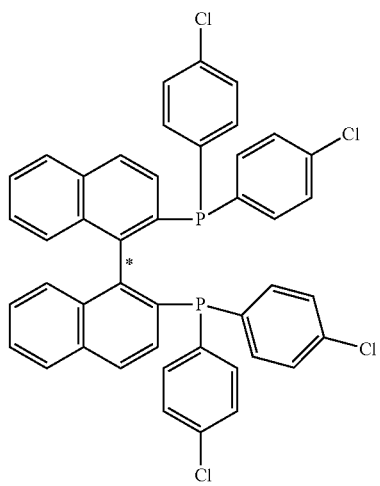

(Sp,R)-Mandyphos or
a mixture thereof, and
(2) an optically active form of a compound represented by the formula:

(X)

wherein the bond marked with * is a chiral axis.

* * * * *